United States Patent
Duffy et al.

(10) Patent No.: US 6,364,845 B1
(45) Date of Patent: Apr. 2, 2002

(54) METHODS FOR DIAGNOSING VISUOSPATIAL DISORIENTATION OR ASSESSING VISUOSPATIAL ORIENTATION CAPACITY

(75) Inventors: Charles J. Duffy, Perinton; Sheldon J. Tetewsky, Rochester, both of NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/397,400

(22) Filed: Sep. 16, 1999

Related U.S. Application Data
(60) Provisional application No. 60/100,759, filed on Sep. 17, 1998.

(51) Int. Cl.[7] .............................................. A61B 13/00
(52) U.S. Cl. ......................... 600/558; 351/200; 128/898
(58) Field of Search ................................ 600/544, 545, 600/558; 351/200, 201, 203, 205, 222; 1208/898

(56) References Cited
U.S. PATENT DOCUMENTS

| | | | | |
|---|---|---|---|---|
| 4,953,968 A | * | 9/1990 | Sherwin et al. | 351/211 |
| 5,474,081 A | * | 12/1995 | Livingstone et al. | 600/544 |
| 5,485,230 A | * | 1/1996 | Zimmerman | 351/239 |
| 5,825,460 A | * | 10/1998 | Kohayakawa | 351/237 |
| 5,846,207 A | * | 12/1998 | Rosenfeld | 600/544 |
| 5,920,374 A | * | 7/1999 | Vaphiades et al. | 351/237 |
| 5,983,129 A | * | 11/1999 | Cowan et al. | 600/544 |
| 6,045,515 A | * | 4/2000 | Lawton | 600/558 |
| 6,057,810 A | * | 5/2000 | Roell et al. | 345/8 |

* cited by examiner

Primary Examiner—Eric F. Winakur
Assistant Examiner—Charles Marmor, II
(74) Attorney, Agent, or Firm—Nixon Peabody LLP

(57) ABSTRACT

The present invention relates to a method for diagnosing visuospatial disorientation or assessing visuospatial orientation capacity in a subject including conducting an optic flow test on the subject, recording results of the test, and comparing the results of the test against a threshold for optic flow perception. The present invention also relates to a method for diagnosing visuospatial disorientation or assessing visuospatial orientation capacity in a subject including conducting an optic flow test on the subject, conducting at least one optic perception and interpretation test other than an optic flow test on the subject, recording results of the optic flow test and the at least one optic perception and interpretation test, making a first comparison of the results of the optic flow test against a threshold for optic flow perception, and making a second comparison of the results of the at least one optic perception and interpretation test against a threshold for the at least one optic perception and interpretation test. Another aspect of the present invention is a method for diagnosing visuospatial disorientation or assessing visuospatial orientation capacity in a subject including conducting an optic flow test on the subject, measuring brain wave responses to record an evoked potential in response to the optic flow test, and comparing the evoked potential against a threshold for optic flow perception. The present invention is also related to a method for enhancing visuospatial orientation capacity in a subject which includes presenting optic flow stimuli on a device to provide a sense of self-movement.

45 Claims, 13 Drawing Sheets

OBSERVER MOVEMENT
FORWARD SELF-MOVEMENT

RADIAL PATTERN OF OPTIC FLOW
FORWARD SELF-MOVEMENT

OBSERVER MOVEMENT
RIGHTWARD SELF-MOVEMENT

RADIAL PATTERN OF OPTIC FLOW
RIGHTWARD SELF-MOVEMENT

RECOGNITION BY DELAYED MATCH TO SAMPLE
SHAPE RECOGNITION

OPTIC FLOW RECOGNITION

DELAY
☐ 250 ms
▨ 500 ms
▧ 750 ms

NO SUPERIMPOSITION
CENTER OF MOTION - LEFT

NO SUPERIMPOSITION
CENTER OF MOTION - RIGHT

RANDOM SUPERIMPOSITION
CENTER OF MOTION - LEFT

RANDOM SUPERIMPOSITION
CENTER OF MOTION - RIGHT

STATIC SUPERIMPOSITION
CENTER OF MOTION - LEFT

STATIC SUPERIMPOSITION
CENTER OF MOTION - RIGHT

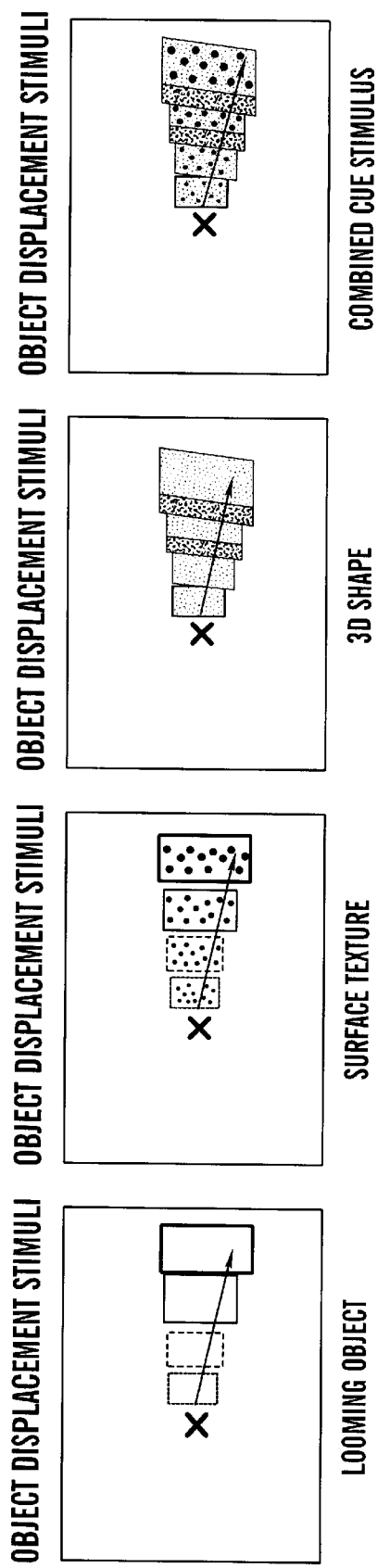

METHODS FOR DIAGNOSING VISUOSPATIAL DISORIENTATION OR ASSESSING VISUOSPATIAL ORIENTATION CAPACITY

This application claims the benefit of U.S. Provisional Patent Application Serial No. 60/100,759, filed Sep. 17, 1998.

This invention was made in part with government support under Grant No. 5P30-AG08665 from th e National Institutes of Heal th. The U.S. government may have certain rights in the invention.

FIELD OF THE INVENTION

The present invention relates to methods for diagnosing visuospatial disorientation or assessing visuospatial orientation capacity and their use in diagnosing neurodegenerative diseases. The present invention also relates to a method for enhancing visuospatial orientation in a subject.

BACKGROUND OF THE INVENTION

Visuospatial disorientation is the inability to perceive, recall, or navigate through the structured environment surrounding, the individual. It includes topographagnosia (the failure to recognize environmental structure) (Holmes, "Disturbances of Vision by Cerebral Lesions," *British J. of Ophthalmology*, 2:353–384 (1918); Brain, "Visual Disorientation With Special Reference to Lesions of the Right Cerebral Hemisphere," *Brain*, 64:244–272 (1941); Critchley, *The Parietal Lobes*, New York, Hafner Publishing Co. (1953)) and is thought to rely on dorsal stream occipito-parietal visual pathways (Mountcastle et al., *The Mindful Brain: Cortical Organization and the Group-Selective Theory of Higher Brain Function*, Cambridge, Mass., MIT Press (1978); Ungerleider et al., "Two Cortical Visual Systems," In: *Analysis of Visual Behavior*, Ingle et al., eds., Cambridge, MIT Press, pp. 549–586 (1982)).

Damage to parieto-occipital cortex has long been associated with the syndrome of visuospatial disorientation (Holmes, "Disturbances of Vision By Cerebral Lesions," *British Journal of Ophthalmology*, 2:353–384(1918), Critchley, "The Parietal Lobes," New York, Hafner Publishing Co., (1953)). More recently, this syndrome has been recognized as a common component of behavioral impairment in Alzheimer's disease ("AD") (Cogan, "Visual Disturbances With Focal Progressive Dementing Disease," *American Journal of Ophthalmology*, 100:68–72 (1985), Levine et al., "The Visual Variant of Alzheimer's Disease: A Clinicopathologic Case Study," *Neurology*, 305–313 (1993)). AD patients with prominent visuospatial disorientation show neuropathological evidence of greater disease impact on parieto-occipital areas (Hof et al., "Balint's Syndrome in Alzheimer's Disease: Specific Disruption of the Occipito-Parietal Visual Pathway," *Brain Research*, 493:368–375 (1989), Hof et al., "Quantitative Analysis of a Vulnerable Subset of Pyramidal Neurons in Alzheimer's Disease: II. Primary and Secondary Visual Cortex," *The Journal of Comparative Neurology*, 301:55–64 (1990)). In addition, functional imaging studies have linked the visuospatial disorientation of AD to metabolic changes in parieto-occipital cortex (Kiyosawa et al., "Alzheimer's Disease with Prominent Visual Symptoms Clinical and Metabolic Evaluation," *Ophthalmology*, 96:1077–1086 (1989), Pietrini et al., "A Longitudinal Positron Emission Tomography Study of Cerebral Glucose Metabolism in Patients With Alzheimer's Disease and Prominent Visual Impairment," *Advances in the Biosciences*, 87:69–71 (1993)).

Visuospatial disorientation can occur either as an isolated syndrome in a distinct presentation of AD (Cogan, "Visual Disturbances With Focal Progressive Dementing Disease," *American J. of Ophthalmology*, 11:68–72 (1985)), or with other impairments in the context of typical AD (Becker et al., "Neuropsychological Function In Alzheimer's Disease. Pattern of Impairment and Rates of Progression," *Arch. Neurology*, 45:263–268 (1988); Levine et al., "The Visual Variant of Alzheimer's Disease: A Clinicopathologic Case Study," *Neurology*, 43:305–313 (1993)). While some normal elderly subjects show aspects of visuospatial disorientation (Flicker et al., "Equivalent Spatial-Rotation Deficits in Normal Aging and Alzheimer's Disease," *J. of Clinical & Exp. Neuropsychology*, 10:294–300 (1988); Lipman et al., "Adult Age Differences in Memory Routes: Effects of Instruction and Spatial Diagram," *Psychology and Aging*, 7:434–442 (1992)), it is a robust finding in 39% of patients with AD (Henderson et al., "Spatial Disorientation in Alzheimer's Disease," *Arch. Neurol.*, 46:391–394 (1989)) who often first complain of spatial confusion and at autopsy have posterior cortical atrophy (PCA) (Benson et al., "Posterior Cortical Atrophy," *Arch. Neurol.*, 45:789–793 (1988)). Convincing evidence of this disorder comes from studies of patients with visuospatial disorientation but no memory impairment, who later develop typical AD (Kaskie et al., "Visuospatial Deficit in Dementia of the Alzheimer Type," *Arch. Neurol.*, 52:422–425 (1995); Butter et al., "Visual-Spatial Deficits Explain Visual Symptoms in Alzheimer's Disease," *Am. J. Ophthalmology*, 122:97–105 (1996)). These patients can be contrasted to AD without visual complaints and verbal, but not spatial, impairments (Binetti et al., "Disorders of Visual and Spatial Perception of the Early Stage of Alzheimer's Disease," *Annals of the NY Academy of Sciences*, 777:221–225 (1996)).

Visuospatial AD must be distinguished from primary visual dysfunction in the setting of AD. AD associated losses of visual acuity, contrast sensitivity, and visual fields are associated with optic atrophy with abnormal visual evoked potentials (VEPs) (Sadun et al., "Assessment of Visual Impairment in Patients With Alzheimer's Disease," *Am. J. of Ophthalmology*, 104:113–120 (1987)). But many AD patients with prominent visual complaints have normal electroretinograms (ERGs) and VEPs (Rizzo et al., "A Human Visual Disorder Resembling Area V4 Dysfunction in the Monkey," *Neurology*, 42:1175–1180 (1992)) and profiles of visual impairment that suggest dysfunction in visual association cortex (Cronin-Golomb et al., "Visual Dysfunction in Alzheimer's Disease Relation to Normal Aging," *Annals of Neurology*, 29:41–52 (1991)). These patients have visuospatial impairments, in the absence of verbal-memory impairments, and fit the neuropsychological profile of posterior cerebral involvement with the preservation of other areas (Furey-Kurkjian et al., "Visual Variant of Alzheimer's Disease: Distinctive Neuropsychological Features," *Neuropsychology*, 10:294–300 (1996)).

The histopathology of AD is most evident in limbic areas, but the greatest cortical involvement is in parietotemporal association areas (Brun et al., "Distribution of Cerebral Degeneration in Alzheimer's Disease," *Arch. Psychiat. Nervenkr.*, 223:15–33 (1976); Brun et al., "Region Pattern of Degeneration in Alzheimer's Disease: Neuronal Loss and Histopathological Grading," *Histopathology*, 5:549–564 (1981); Mountjoy et al., "Cortical Neuronal Counts in Normal Elderly Controls and Demented Patients," *Neurobiology of Aging*, 4:1–11 (1983)) with neurofibrillary tangles (NFTs) increasing from primary to tertiary visual areas especially effecting corticocortical projection neurons (Lewis et al., "Laminar and Regional Distributions of Neurofibrillary Tangles and Neuritic Plaques in Alzheimer's Disease: A Quantitative Study of Visual and Auditory Cortices," *The Journal of Neuroscience*, 7:1799–1808 (1987); Arnold et al., "The Topographical and Neuroanatomical Distribution of Neurofibrillary Tangles and Neuritic Plaques in the Cerebral Cortex of Patients With Alzheimer's Disease," 1:103–116 (1991)). In visual AD the pathology is more concentrated in visual areas (Hof et al., "Balint's Syndrome in Alzheimer's Disease: Specific Disruption of the Occipito-Parietal Visual Pathway," *Brain Research*, 493:368–375 (1989); Hof et al., "Quantitative Analysis of a Vulnerable Subset of Pyramidal Neurons in Alzheimer's Disease: II. Primary and Secondary Visual Cortex," *The Journal of Comparative Neurology*, 301:55–64 (1990)), especially in neurons with intracortical projections to visual association areas, potentially creating a functional disconnection in the occipito-parietal visual pathway (Hof et al., "Quantitative Analysis of a Vulnerable Subset of Pyramidal Neurons in Alzheimer's Disease: II. Primary and Secondary Visual Cortex," *The Journal of Comparative Neurology*, 301:55–64 (1990)). This posterior cortical localization is confirmed by 18-fluorodeoxyglucose positron emission tomography (18FDG-PET) studies showing a 35–40% decrease in occipito-parietal blood flow relative to AD patients without visual symptoms (Kiyosawa et al., "Alzheimer's Disease With Prominent Visual Symptoms. Clinical and Metabolic Evaluation," *Ophthalmology*, 96:1077–1086 (1989)) with preserved flow in the frontal cortical areas most commonly effected in AD (Pietrini et al. "A Longitudinal Position Emission Tomography Study of Cerebral Glucose Metabolism in Patients With Alzheimer's Disease and Prominent Visual Impairment," *Advances in the Biosciences*, 87:69–71 (1993); Pietrini et al., "Preferential Metabolic of Visual Cortical Areas in a Subtype of Alzheimer's Disease: Clinical Implications," *American Journal of Psychiatry*, 153:1261–1268 (1996)).

Normal elderly and AD subjects show impaired visual motion detection with thresholds substantially higher than those of young normals (Mendola et al., "Prevalence of Visual Deficits in Alzheimer's Disease," *Optometry and Vision Science*, 72:155–167 (1995)). Discrimination thresholds for the direction of visual motion also increase with age, doubling from age 30 to 80 years, with dramatic increases in patients with AD (Trick et al., "Visual Sensitivity of Motion: Age-Related Changes and Deficits in Senile Dementia of the Alzheimer Type," *Neurology*, 41:1437–1440 (1991)). Gilmore (Gilmore et al., "Motion Perception and Alzheimer's Disease," *Journal of Gerontology*, 49:P52–7 (1994)) found a strong correlation between visual motion thresholds and cognitive impairments in AD and evidence of a relationship between visual motion thresholds and visuospatial impairments (Gilmore et al., "Motion Perception and Aging." *Psychology and Aging*, 7:654–600 (1992)).

These findings demand consideration of the possibility that visual motion impairments in aging and AD might reflect an ocular visual disorder which blocks central access to visual motion signals. This issue has been clarified by studies of the multiple visual impairments of AD (Cronin-Golomb et al., "Visual Dysfunction Alzheimer's Disease Relation to Normal Aging," *Annals of Neurology*, 29:41–52 (1991)) showing that object recognition deficits are accounted for by losses in acuity, color discrimination, contract sensitivity, etc., but visuospatial deficits can not be so explained (Cronin-Golomb et al., "Visual Dysfunction Predicts Cognitive Deficits in Alzheimer's Disease," *Optometry and Vision Science*, 72:168–176 (1995)). The cortical origin of the visual motion detection deficit in AD is supported by data showing that they have impaired visual motion perception, but normal motion thresholds for inducing optokinetic nystagmus (Silverman et al., "Dissociation Between the Detection and Perception of Motion in Alzheimer's Disease," *Neurology*, 44:1814–1818 (1994)).

Functional imaging has identified the human visual motion cortex, and suggested that the visuospatial disorientation of AD is attributable to a disorder in this system. Visual motion activation in normal humans has been localized to the inferior parietal and superior temporal gyri of occipito-parietal cortex using $H_2^{15}O$-PET (Dupont et al., "Many Areas in the Human Brain Respond to Visual Motion," *Journal of Neurophysiology*, 72:1420–1424 (1994); de Jong et al., "The Cerebral Activity Related to the Visual Perception of Forward Motion in Depth," *Brain*, 117:1039–1054 (1994); Cheng et al., "Human Cortical Regions Activated By Wide-Field Visual Motion: An $H_2^{15}O$-PET Study," *Journal of Neurophysiology*, 74:413–427 (1995) (Abstract)) and functional magnetic resonance imaging (fMRI). This region is activated in visuospatial perception tasks studied by PET (Haxby et al., "The Functional Organization of Human Extrastriate Cortex: A PET-rCBF Study of Selective Attention to Faces and Locations," *The Journal of Neurosciences*, 14:6336–6353 (1994)) and fMRI (Aguirre et al., Environmental Knowledge is Subserved by Separable Dorsal/Ventral Neural Areas," *The Journal of Neuroscience*, 17:2512–2518 (1997)), with visual AD subjects showing impaired activation of these occipito-parietal areas during visual motion processing (Mentis et al., "Visual Cortical Dysfunction in Alzheimer's Disease Evaluated With a Temporally Graded "Stress Test" During PET," *Am. J. Psychiatry*, 153:32–40 (1996)). However, PET studies also show that when spatial memory is engaged, a critical aspect of spatial behavior in the elderly (Simon et al., "Spatial Cognition and Neighborhood Use: The Relationship in Older Adults," *Psychology and Aging*, 7:389–394 (1992)), there is also hippocampal and parahippocampal activation (Aguirre et al., "The Parahippocampus Subserves Topographical Learning in Man," *Cerebral Cortex*, 6:823–829 (1996)). Thus, PET studies show the complexities of spatial behavior, not contradicting the hypothesized role of visual motion processing, but reminding us that hippocampal memory of a cognitive map (O'Keefe et al., *The Hippocampus as a Cognitive Map*, Clarendon, Oxford (1978)) is another element of spatial orientation that might be susceptible to impairment in AD.

Gibson (Gibson, *The Perception of the Visual World*, Boston, Houghton Mifflin (1950); Optical Motions and Transformations as Stimuli for Visual Perception," *Psychological Review*, 64:288–295 (1957)) first emphasized that spatial orientation relies on the processing of the patterned visual motion of optic flow which surrounds a moving observer, and is accompanied by the visual motion of discrete objects, as cues about self-movement and the three-dimensional structure of the environment. Subsequently, others have used geometric and computational analyses to confirm that visual motion is a rich source of information about observer movement through extrapersonal space (Lee, "The Optic Flow Field: The Foundation of Vision." *Philosophical Transactions of the Royal Society of London— Series B: Biological Sciences*, 290:169–179 (1980); Heeger, "Model for the Extraction of Image Flow," *J. Opt. Soc. Am. A.*, 4:1455–1471 (1987); Perrone, "A Simple Technique For Optical Flow Estimation," *J. Opt. Soc. Am. A.*, 7:264–278. (1990); Fermuller et al., "Direct Perception of Three-Dimensional Motion From Patterns of Visual Motion,"

*Science*, 270:1973–1976 (1995)) and the three-dimensional structure of the visual environment (Koenderink et al., "Invariant Properties of the Motion Parallax Field Due to the Movement of Rigid Bodies Relative to an Observer," *Optica Acta*, 22:773–791 (1975); Rogers et al., "Motion Parallax as an Independent Cue for Depth Perception," *Perception*, 8:125–134 (1979); Braunstein et al., "Shape and Depth Perception From Parallel Projections of Three-Dimensional Motion," *J. Exp. Psych.*, 10:749–760 (1984); Simpson, "Optic Flow and Depth Perception," *Spatial Vision*, 7:35–75 (1993)).

Psychophysical analyses of human performance have shown that visual motion cues are accessed in tests of self-movement perception (Warren et al., "Direction of Self-Motion is Perceived From Optical Flow," *Nature*, 336:162–163 (1988); Banks et al., "Estimating Heading During Real and Simulated Eye Movements," *Vision Research*, 36:431–443 (1996); Stone et al., "Human Heading Estimation During Visually Simulated Curvilinear Motion," *Vision Research*, 37:573–590 (1997)), although the exact nature of the underlying perceptual strategies remains a subject of intense scrutiny (Rieger et al., "Processing Differential Image Motion," *J. Opt. Soc. Am. A.*, 2:354–359 (1985); Stone et al., "Human Heading Perception Cannot Be Explained Using a Local Differential Motion Algorithm," *Invest. Oplhthalmol. Vis. Sci.*, 34:1229 (1993); Lappe et al., "Neural Network for the Processing of Optic Flow From Ego-Motion in Higher Mammals," *Neural Computation*, 5:374–391 (1993)). Visual motion has also been shown to cue observers about the layout of the visual environment (Lee, "A Theory of Visual Control of Braking Based on Information About Time-To-Collision," *Perception*, 5:437–459 (1976); Cornilleau-Peres et al., "Stereo-Motion Cooperation and the Use of Motion Disparity in the Visual Perception of 3-D Structure," *Perception & Psychophysics*, 54:223–239 (1993); Regan et al., "Visual Processing of Looming and Time to Contact Throughout the Visual Field," *Vision Research*, 35:1845–1857 (1995)), to guide locomotion (Lee, "A Theory of Visual Control of Braking Based on Information About Time-To-Collision," *Perception*, 5:437–459 (1976); Lee et al., "Visual Control of Locomotion," *Scand. J. Psychol.*, 18:224–230 (1977)), and reaching (Lee et al., "Visual Timing of Interceptive Behavior," In: *Brain Mechanisms and Spatial Vision*, lugle et al., eds., Dordrecht, The Netherlands Martins Nijhoff (1985); Savelsbergh et al., "The Visual Guidance of Catching," *Exp. Brain Res.*, 93:148–156 (1993)). Furthermore, visual motion can have so profound an effect on orienting mechanisms that a variety of illusions of self-movement and spatial disorientation can be triggered by visual motion stimuli (Held et al., "Characteristics of Moving Visual Scenes Influencing Spatial Orientation," *Vision Res.*, 15:357–364 (1975); Berthoz et al., "Perception of Linear Horizontal Self-Motion Induced by Peripheral Vision (Linearvection) Basic Characteristics and Visual-Vestibular Interactions," *Experimental Brain Research*, 23:471–489 (1975); Ohmi et al., "Circular Vection as a Function of Foreground-Background Relationships," *Perception*, 16:17–22 (1987)).

Neurophysiologic studies have demonstrated that primate visual cortex neurons encode the large visual motion patterns of optic flow (Saito et al., "Integoration of Direction Signals of Image Motion in the Superior Temporal Sulcus of the Macaque Monkey," *Journal of Neuroscience*, 6:145–157 (1986); Tanaka et al., "Underlying Mechanisms of the Response Specificity of Expansion/Contraction and Rotation Cells in the Dorsal Part of the Medial Superior Temporal Area of the Macaque Monkey," *J. Neurophysiol.*, 62:642–656 (1989); Duffy et al., "Sensitivity of MST Neurons to Optic Flow Stimuli. I. A Continuum of Response Selectivity to Large-Field Stimuli," *J. Neurophysiol.*, 65:1329–1345 (1991); Duffy et al., "Sensitivity of MST Neurons to Optic Flow Stimuli. II. Mechanisms of Response Selectivity Revealed By Small-Field Stimuli." *J. Neurophysiol.*, 65:1346–1359 (1991); Orban et al., "First-Order Analysis of Optical Flow in Monkey Brain," *Proceedings of the National Academy of Sciences of the United States of America*, 89:2595–2599 (1992); Graziano et al., "Tuning of MST Neurons to Spiral Motion," *J. Neurosci.*, 14:54–67 (1994)) responding to the direction of self-movement and the environmental layout (Duffy et al., "Response of Monkey MST Neurons to Optic Flow Stimuli With Shifted Centers of Motion," *J. Neurosci.*, 15:5192–5208 (1995); Duffy et al., "Planar Directional Contributions to Optic Flow Responses in MST Neurons," *J. Neurophysiol.*, 77:782–796 (1997); Duffy et al., "Medial Superior Temporal Area Neurons Respond to Speed Patterns in Optic Flow," *J. Neurosci.*, 17:2839–2851 (1997)) while integrating visual and vestibular signals about orientation (Duffy, "Real Movement Responses of Optic Flow Neurons in MST," *Society for Neuroscience Abstracts*, 22:1692 (1996) (Abstract)). Neuronal mechanisms for the analysis of visual object motion have shown selective responses to movement along a specific trajectory (Motter et al., "Functional Properties of Parietal Visual Neurons: Mechanisms of Directionality Along a Single Axis," *J. Neurosci.*, 7:154–176 (1987); Steinmetz et al., "Function Properties of Parietal Visual Neurons: Radial Organization of Directionalities Within the Visual Field," *J. Neurosci.*, 7:177–191 (1987)) of relative object motion (Tanaka et al., "Analysis of Object Motion in the Ventral Part of the Medial Superior Temporal Area of the Macaque Visual Cortex," *J. Neurophysiol.*, 69:128–142 (1993)) regardless of the specific form of the object (Geesaman et al., "The Analysis of Complex Motion Patterns By Form/Cue Invariant MSTd Neurons," *J. Neurosci.*, 16:4716–4732 (1996)) even when embedded in conflicting patterns of optic flow (Logan et al., "MST Neurons Integrate Visual Cues From Self- and Object-Motion." *Soc. Neurosci. Abstr.*, 23:1126 (1997) (Abstract)). These neurons might interact with cortical representations of head direction (Chen et al., "Head Direction Cells in Rat Posterior Cortex. I. Anatomical Distribution and Behavioral Modulation," *Exp. Brain Res.*, 101:8–23 (1994); Chen et al., Head Direction Cells in Rat Posterior Cortex. II. Contributions of Visual and Ideothetic Information to the Directional Firing," *Exp. Brain Res.*, 101:23–34 (1994)) and body rotation (McNaughton et al., "Cortical Representation of During Unrestrained Spatial Navigation in the Rat," *Cerebral Cortex*, 4:27–39 (1994)) to create a neural signal driving memory mechanisms for spatial orientation (O'Keefe et al., *The Hippocampus as a Cognitive Map*, Clarendon, Oxford (1978)) which rely on place sensitive hippocampal neurons for spatial memory (Bostock et al., "Experience-Dependent Modifications of Hippocampal Place Cell Firing," *Hippocampus*, 1:193–206 (1991); Sharp et al., "Influences of Vestibular and Visual Motion Information on the Spatial Firing Patterns of Hippocampal Place Cells," *J. Neurosci.*, 15:173–189 (1995)) to create an internal map of extrapersonal space in the context of relevant visuospatial cues (Mueller et al., "Visually Induced Vertical Self-Motion Sensation is Altered in Microgravity Adaptation," *J. Vestibular Research*, 4:161–167 (1994); Gothard et al., "Dynamics of Mismatch Correction in the Hippocampal Ensemble Code for Space: Interaction Between Path Integration and Environmental Cues," *J. Neurosci.*, 60:8027–8040 (1996); O'Keefe et al., "Geometric Determinants of the Place Fields of Hippocampal Neurons," *Nature*, 381:425–428 (1996)).

Single neuron recordings in the dorsal extrastriate visual cortex of monkeys have shown selective responses to the visual motion patterns of optic flow (Tanaka et al., "Underlying Mechainisms of the Response Specificity of Expansion/Contraction and Rotation Cells in the Dorsal Part of the Medial Superior Temporal Area of the Macaque Monkey," *J. Neurophysiol*, 62:642–656 (1989), Duffy et al., "Sensitivity of MST Neurons to Optic Flow Stimuli. II. Mechanisms of Response Selectivity Revealed by Small-Field Stimuli." *Journal of Neurophysiology*, 65:1346–1359 (1991)). Neurons in these areas are activated by visual cues about heading direction (Duffy et al., "Response of Monkey MST Neurons to Optic Flow Stimuli With Shifted Centers of Motion," *Journal of Neuroscience*, 15:5192–5208 (1995)) and environmental structure (Duffy et al., "Medial Superior Temporal Area Neurons Respond to Speed Patterns in Optic Flow," *Journal of Neuroscience*, 17:2839–2851 (1997)) that are embedded in the optic flow field. These dorsal extrastriate areas of monkey cerebral cortex are homologous to parts of human parieto-occipital cortex (Haxby et al., "The Functional Organization of Human Extrastriate Cortex: A PET-rCBF Study of Selective Attention to Faces and Locations," *The Journal of Neurosciences*, 14:6336–6353 (1994), Sereno et al., "Borders of Multiple Visual Areas in Humans Revealed by Functional magnetic Resonance imaging," *Science*, 268:889–893 (1995)) containing multiple centers for visual motion processing (Dupont et al., "Many Areas in the Human Brain Respond to Visual Motion," *Journal of Neurophysiology*, 72:1420–1424 (1994), de Jong et al., "The Cerebral Activity Related to the Visual Perception of Forward Motion in Depth, *Brain*, 117:1039–1054 (1994)).

Gibson first emphasized that the visual motion in optic flow influences postural control (Gibson, "The Perception of the Visual World," Boston, Houghton Mifflin (1950)). Early studies integrating the posturography with optic flow stimuli demonstrated visuo-postural reflexes elicited by visual motion in the central visual field (Brandt et al., "Differential Effects of Central Versus Peripheral Vision on Egocentric and Exocentric Motion Perception," *Exp. Brain Res.*, 16:476–491 (1973), Lee, "The Optic Flow Field: The Foundation of Vision," *Philosophical Transactions of the Royal Society of London—Series B: Biological Sciences*, 290:169–179 (1980); Lestienne et al., "Postural Readjustments Induced by linear Motion of Visual Scenes," *Exp. Brain Res.*, 28:363–384 (1977)). More recent work has explored the visual stimulus parameters that influence the direction, amplitude, and temporal aspects of visuo-postural responses (Stoffregen, "The Role of Optical Velocity in the Control of Stance," *Perception & Psychophysics*, 39:355–360 (1986); Asten et al., "Postural Adjustments Induced by Simulated Motion of Differently Structured Environments," *Exp. Brain Res.*, 73:371–383 (1988); Gielen et al., "Postural Responses to Simulated Moving Environments are not Invariant for the Direction of Gaze," *Exp. Brain Res.*, 79:167–174 (1990)). Previous work on postural control in monkeys has documented optic flow induced responses, potentially under the influence of visual motion processing in cortical area medial superior temporal ("MST") (Duffy et al., "Optic Flow, Posture, and the Dorsal Visual Pathway," in *Perception. Memory, and Emotion: Frontiers in Neuroscience*, Ono et al., eds., Elsevier, N.Y., pp. 63–77 (1996)).

Vision increasingly controls postural stability in aging, possibly because of common losses in proprioceptive and vestibular input (Pyykko et al., "Postural Control in Elderly Subjects," *Age and Aging*, 19:215–221 (1990); Lord et al., "Visual Field Dependence in Elderly Fallers and Non-fallers," *Int'l. J. Aging and Human Development*, 31:267–277 (1990)) interacting with the normal dominance of vision in the postural control hierarchy (Lee, "The Optic Flow Field: The Foundation of Vision," *Philosophical Transactions of the Royal Society of London—Series B: Biological Sciences*, 290:169–179 (1980)). This reliance on vision has been related to the risk of falling in the elderly, especially with unstable support surfaces (Maki et al., "Aging and Postural Control: A Comparison of Spontaneous- and Induced-Sway Balance Tests," *J. Am. Geriatrics Society*, 38:1–9 (1990);Whipple et al., Altered Sensory Function and Balance in Older Persons," *The Journal of Gerontology*, 48:71–76 (1993)). Specific conditions that destabilize the elderly have found disorders of sensory integration and motor coordination (Alexander, "Postural Control in Older Adults," *J. Am. Geriatrics Society*, 42:93–108 (1994); Baloh et al., "Comparison of Static and Dynamic Posturography in Young and Older Normal People," *J. Am. Geriatrics Society*, 42:405–412 (1994)) including forced reliance on the visual motion of optic flow presented in the peripheral visual field (Wade et al., "Optical Flow, Spatial Orientation, and the Control of Posture in the Elderly," *J. Gerontology*, 50B:P51–P58 (1995)).

Visual stimuli have an exaggerated influence on postural control in patients with Parkinson's disease (PD) contributing to their freezing in door ways and other visual barriers (Flowers, "Visual "Closed-Loop" and "Open-Loop" Characteristics of Voluntary Movement in Patients with Parkinsonism and Intention Tremor," *Brain*, 99:269–310 (1976); Cooke et al., "Increased Dependence on Visual Information for Movement Control in Patients with Parkinson's Disease," *Canadian Journal of Neurological Sciences*, 5:413–415 (1978)). Optic flow induced postural responses are increased in PD but not in cerebellar extrapyramidal disorders (Bronstein et al., "Visual Control of Balance in Cerebellar and Parkinsonian Syndromes," *Brain*, 113:767–779 (1990)). This effect does not reflect the loss of peripheral proprioceptive or vestibular input in these patients (Pastor et al., "Vestibular Induced Postural Responses in Parkinson's Disease," *Brain*, 116:1177–1190 (1993)). In contrast, patients with Alzheimer's disease (AD) show postural instability only when confronted with unstable support surfaces with fall risks that are not clearly related to scores on a variety of cognitive tests (Alexander et al., "Maintenance of Balance, Gait Patterns, and Obstacle Clearance in Alzheimer's Disease," *Neurology*, 45:908–914 (1995)).

A need continues to exist, however, to elucidate the neurobehavioral mechanisms of visuospatial disorientation in aging and neurodegenerative diseases, such as AD. More particularly, a need exists to characterize the contributions of optic flow to visuospatial orientation and, as a result, neurodegenerative diseases. The present invention is directed to overcoming the above-noted deficiencies in the prior art.

SUMMARY OF THE INVENTION

The present invention relates to a method for diagnosing visuospatial disorientation or assessing visuospatial orientation capacity in a subject including conducting an optic flow test on the subject, recording results of the optic flow test, and comparing the results of the optic flow test against a threshold for optic flow perception.

The present invention also relates to a method for diagnosing visuospatial disorientation or assessing visuospatial orientation capacity in a subject including conducting an optic flow test on the subject, conducting at least one optic perception and interpretation test other than an optic flow test on the subject, recording results of the optic flow test and the at least one optic perception and interpretation test, making a first comparison of the results of the optic flow test against a threshold for optic flow perception, and making a second comparison of the results of the at least one optic perception and interpretation test against a threshold for the at least one optic perception and interpretation test.

Another aspect of the present invention is a method for diagnosing visuospatial disorientation or assessing visuospatial orientation capacity in a subject including conducting an optic flow test on the subject, measuring brain wave responses to record an evoked potential in response to the optic flow test, and comparing the evoked potential against a threshold for optic flow perception.

The present invention also relates to a method for enhancing visuospatial orientation in a subject which includes presenting optic flow stimuli on a device to provide a sense of self-movement.

The methods of the present invention allow for the early detection of neurobehavioral impairments, such as Alzheimer's disease. Such early detection is an improvement over the methods of diagnosis in the prior art and allows treatment to be started at an earlier stage of the disease.

In addition, these methods allow the visuospatial orientation capacity of a subject to be assessed for a number of purposes including identifying subjects who will be safe drivers and identifying those with an enhanced visuospatial orientation capacity for employment in certain fields, e.g., pilots.

A further advantage of the present invention is that the visuospatial orientation of a user of a device, such as a heads-up display used by pilots, can be enhanced by simulating movement to allow the user to better perform a job or activity. dr

BRIEF DESCRIPTION OF THE DRAWINGS

FIGS. 5A–D show object displacement stimuli for an object vision test;

DETAILED DESCRIPTION OF THE INVENTION

One embodiment of the present invention relates to a method for diagnosing visuospatial disorientation or assessing visuospatial orientation capacity in a subject including conducting an optic flow test on the subject, recording results of the optic flow test, and comparing the results of the optic flow test against a threshold for optic flow perception.

Figure 1A:
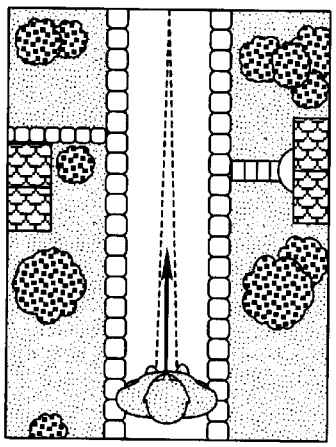
FIGS. 1A–D show the radial pattern of optic flow as a function of observer movement.
Figure 1B:
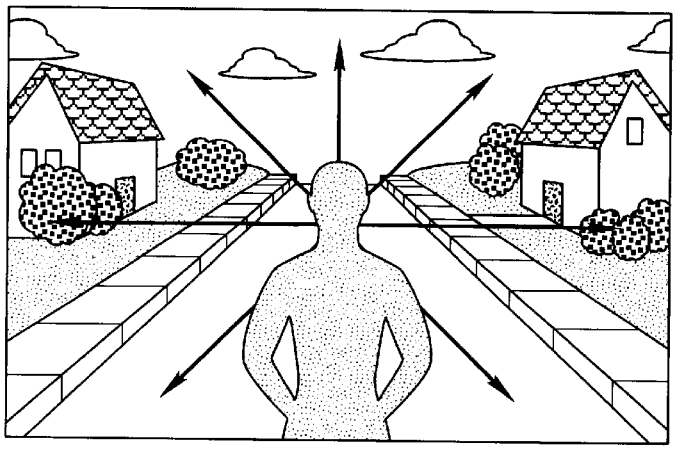
Figure 1C:
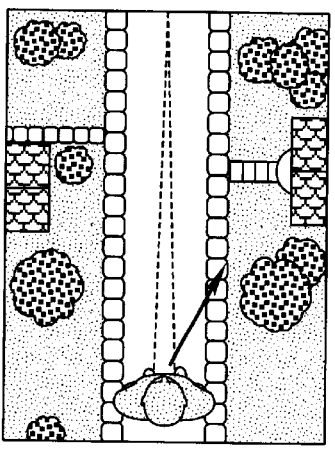
Figure 1D:
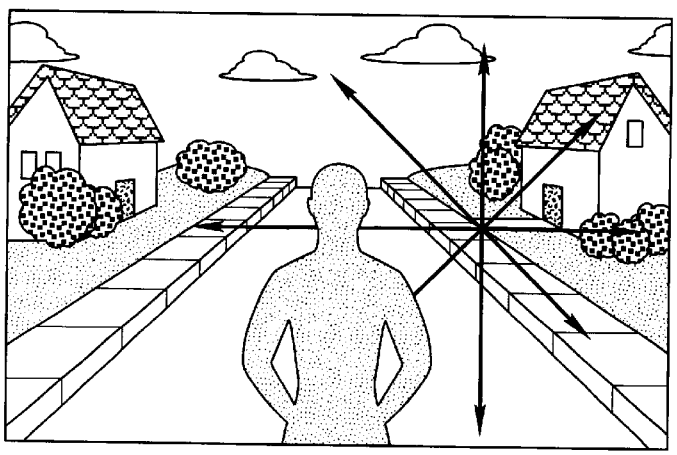

Visuospatial orientation relies greatly on the processing of the patterned visual motion of optic flow that is seen during observer self-movement (Gibson, "The Perception of the Visual World," Boston, Houghton Mifflin (1950), which is hereby incorporated by reference). The radial patterns of optic flow facilitate spatial navigation by indicating the direction of self-movement and the relative position of objects in the environment (Lee, "The Optic Flow Field: The Foundation of Vision," *Philosophical Transactions of the Royal Society of London—Series B: Biological Sciences*, 290:169–170 (1980), Warren et al., "Perceiving Heading in the Presence of Moving Objects," *Perception*, 24:315–331 (1995), which are hereby incorporated by reference). Formal analyses have shown that both of these cues indicate heading (Lee, "The Optic Flow Field: The Foundation of Vision," *Philosophical Transactions of the Royal Society of London—Series B: Biological Sciences*, 290:169–179 (1980); Heeger, "Model for the Extraction of Image Flow," *J. Opt. Soc. Am. A.*, 4:1455–1471 (1987); Perrone, "A Simple Technique for Optical Flow Estimation," *J. Opt. Soc. Am. A.*, 7:264–278 (1990); Fermuller et al., "Direct Perception of Three-Dimensional Motion From Patterns of Visual Motion," *Science*, 270:1973–1976 (1995), which are hereby incorporated by reference) and constitute two orientation strategies: optic flow registers the path of self movement, and object vision monitors relative position. More particularly, referring to FIGS. 1A–D, the radial pattern of optic flow contains a focus of expansion that indicates the observers heading. During forward self-movement in the direction of gaze (FIG. 1A), the observer sees a symmetric, radial pattern of optic flow in which the focus of expansion is at the fixation point (FIG. 1B). During self-movement ahead to the right (FIG. 1C), the observer sees a radial pattern in which the focus of expansion is displaced to the right of gaze (FIG. 1D) to indicate a rightward heading.

Visuospatial disorientation is a prominent feature of aging and neurodegenerative disorders, such as AD, with histopathologic and functional imaging showing greatest impact in occipito-parietal cortex. The clinical, pathologic, and metabolic abnormalities suggest a stable disorder subject to neuropsychological and psychophysical analysis. The devastating nature of spatial disorientation and the increasing population of the elderly in the American population who may be affected by it, implies that this syndrome could become an enormous problem. Further, visual motion processing is impaired in elderly and AD subjects with the severity of this impairment related to the severity of visuospatial disorders. Both of these impairments appear to be the result of cortical deficits referable to occipito-parietal dysfunction.

Neuroscientific analyses have demonstrated that visual motion is a rich source of spatial orientation cues, that are accessed by human observers, probably engaging occipito-parietal neurons that respond to optic flow and object motion. Although not wishing to be bound by theory, these mechanisms may interact with hippocampal place neurons to create spatial memory for use in path integration and landmark recognition strategies of spatial orientation. Thus, visual motion processing may be part of a spatial orientation network that contains cortical and subcortical sites of particular vulnerability to the effects of aging and neurodegenerative diseases.

A variety of different types of optic flow tests, such as an optic flow discrimination test, a visual self-movement interpretation test, an optic flow delayed match test, or an optic flow remembered heading test can be used. Referring to FIGS. 2E–F, an optic flow discrimination test includes a pseudorandom sequence of stimuli in which outward radial patterns are superimposed on a background such as a plurality of dots moving in random directions. Preferably, between 1% and 43% of the dots are in the radial pattern. In this implementation, the outward radial patterns have a focus of expansion 15° to the left or right of center. The visual stimulus is presented to the subject and the subject must determine whether the focus of expansion is on the left or on the right.

A visual self-movement interpretation test is based on the concept of vection—the illusion of self-movement based on a visual flow. Preferably, an optic flow visual self-movement interpretation test includes a pseudorandom sequence of stimuli in which outward radial patterns are superimposed on a background such as a plurality of dots moving in random directions. Preferably, between 1% and 43% of the dots are in the radial pattern. In a more preferred embodiment, the outward radial patterns have a focus of expansion 15° to the left or right of center, and at the more extreme positions of 30° to the left or right of center. The visual stimulus is presented to the subject and the subject must determine the direction of movement simulated by the stimuli.

Figure 3A:
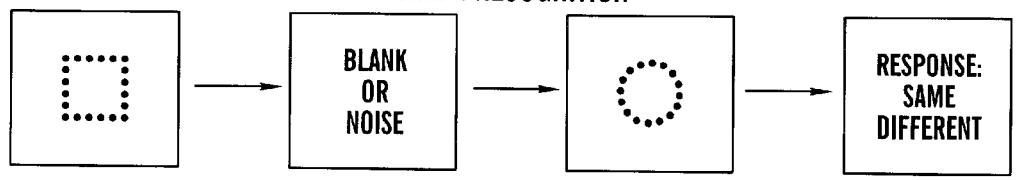
FIGS. 3A–D show shape and optic flow stimuli and results for visual memory tests.
Figure 3B:
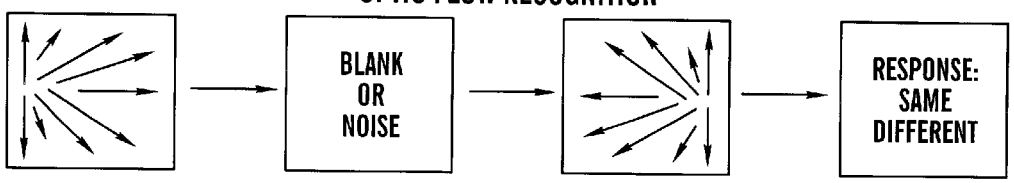

Referring to FIGS. 3A–B, an optic flow delayed match test includes presenting a visual stimulus in which outward radial patterns are superimposed on a background such as a plurality of dots moving in random directions, presenting a blank visual area, and presenting a second visual stimulus. The subject must determine whether the second visual stimulus is the same or different than the first visual stimulus.

Referring to FIG. 4, an optic flow remembered heading test includes a pseudorandom sequence of stimuli in which outward radial patterns are superimposed on a background such as a plurality of dots moving in random directions with varying levels and types of background noise. More preferably, the optic flow stimuli are presented at 100% coherence (no background noise), 50% stationary random dots, or 50% moving random dots. The visual stimulus is presented to the subject and the subject must determine the perceived location of the center of motion of the optic flow stimulus. Although examples of optic flow tests which can be used are disclosed above, other types of optical flow tests may also be used with the present invention.

Test results from the optic flow test are recorded using methods well known to those of ordinary skill in the art, such as by presenting a visual stimulus followed by an indicator produced by a computer to prompt a response by the subject, and receiving and storing the response in the computer, although other methods can be used. For example, in one particular embodiment, test results are recorded as an evoked potential which is the average of brain wave responses to processed stimuli. In this example, recording test results as an evoked potential includes measuring brain wave responses in a subject to the visual stimuli presented to the test subject and then averaging the brain wave responses.

Once the results of the optic flow test are recorded, then they are compared against a threshold for optic flow perception to assess visuospatial orientation capacity. As used herein, a threshold for optic flow perception is defined as the presentation of optic flow stimuli at which subjects achieve approximately 75% correct responses. Preferably, a threshold for optic flow perception is the percentage of dots in a radial pattern ([pattern dots/pattern plus random dots] ×100) at which subjects achieve approximately 75% correct responses.

The method in accordance with one embodiment may also include correlating the comparison of the results of the optic flow test against a threshold for optic flow perception with a profile for a neurodegenerative disorder under conditions effective to diagnose a neurodegenerative disorder. Profiles for neurodegenerative disorders are developed by performing optic flow tests on subjects diagnosed with particular neurodegenerative disorders, such as Alzheimer's disease ("AD"), Parkinson's disease ("PD"), and Lewy Body disease ("LBD"), as well as stroke, traumatic brain injury, and focal tumors or malformations.

One of the advantages of the present invention is that it can be used to identify subjects with normal or increased visuospatial capacity and to monitor visuospatial capacity on an ongoing basis. Subjects with normal or increased visuospatial capacity are more likely to be suitable for employment in certain fields such as pilots and professional drivers. Another advantage of the present invention is that the results of the comparison of the optic flow test against a threshold for optic flow perception can be used to diagnose visuospatial disorientation.

One embodiment of the present invention may also include some additional steps, such as conducting at least one optic perception and interpretation test other than an optic flow test on the subject, recording results of the at least one optic perception and interpretation test, and then comparing the results of the at least one optic perception and interpretation test against a threshold for the at least one optic perception and interpretation test. Suitable tests of optic perception and interpretation other than optic flow tests include tests of spatial navigation, shape discrimination tests, horizontal motion discrimination tests, visuo-postural reflex tests, and object vision tests, although other tests of optic perception and interpretation may also be used.

A test of spatial navigation involves testing a subject's memory regarding a route traveled from point A to point B.

Figure 2A:
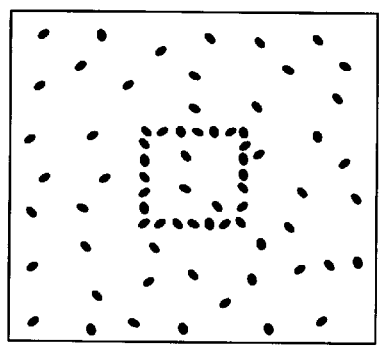
FIGS. 2A–F show visual discrimination stimuli including shape discrimination stimuli (FIGS. 2A–B), horizontal motion stimuli (FIGS. 2C–D), and radial optic flow stimuli (FIGS. 2E–F)
Figure 2B:
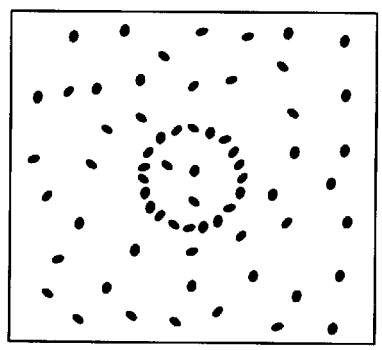

Referring to FIGS. 2A–B, a shape discrimination test includes a pseudorandom sequence of stimuli in which a visual stimulus in the form of a shape, e.g., a square or circle, is superimposed on a background such as stationary dots. Preferably, the shape pattern comprises between 1.2% and 11% of the viewing area. In a preferred embodiment, each stimulus comprises a coherent pattern containing a given percentage of the total number of dots on the screen, the remaining dots being randomly distributed. Static shape stimuli comprise the outlines of circles or squares formed by dots and superimposed on randomly placed stationary dots. The visual stimulus is presented to the subject and the subject must determine the shape in the imbedded pattern.

Figure 2C:
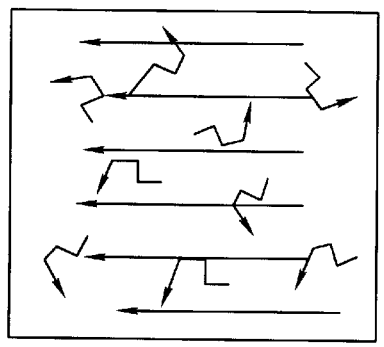
Figure 2D:
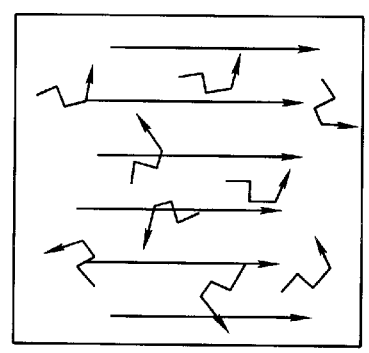
Figure 2E:
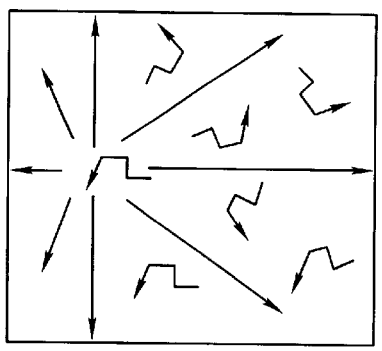
Figure 2F:
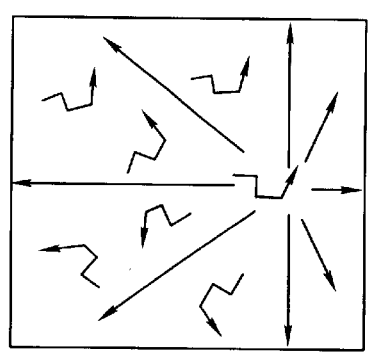

Referring to FIGS. 2C–D, a horizontal motion discrimination test includes a pseudorandom sequence of stimuli in which a leftward or rightward visual stimulus is superimposed on a background such as randomly moving dots. Preferably, the horizontal movement pattern comprises between 1% and 43% of the viewing area. In a preferred embodiment, horizontal motion stimuli contain either leftward or rightward moving dots superimposed on randomly moving dots. The visual stimulus is presented to the subject and the subject must determine the direction of the motion.

A visuo-postural reflex test includes a pseudorandom sequence of stimuli in which circular and radial optic flow visual stimuli are superimposed on a background such as a plurality of dots moving in random directions. Preferably, the radial pattern comprises between 1% and 43% of the viewing area. The visual stimulus is presented to the subject and the postural responses are recorded.

Referring to FIGS. 5A–D, an object vision test includes a pseudorandom sequence of stimuli in which a boundary defined object is superimposed along a horizontal meridian on a uniform background. In subsequent frames the object moves and expands to simulate the scene during subject movement past the object. The subject's heading relative to the object is specified by the ratio of position and size changes. In a preferred embodiment, texture is added to the object's surface as a cue about the subject's relative movement. In another preferred embodiment, three-dimensional shape is added to the object as a cue about the subject's relative movement.

As described above, test results from the optic perception and interpretation test are recorded using methods well known to those of ordinary skill in the art, such as by presenting a visual stimulus followed by an indicator produced by a computer to prompt a response by the subject, and receiving and storing the response in the computer and recording test results as an evoked potential.

Once the results of the at least one optic perception and interpretation test have been recorded, they are compared against a threshold for the at least one optic perception and interpretation test. The results of that comparison along with the results from the comparison of the optic flow test can then be correlated with a profile for a neurodegenerative disorder to diagnose the neurodegenerative disorder.

The present invention also relates to a method for diagnosing visuospatial disorientation or assessing visuospatial orientation capacity in a subject including conducting an optic flow test on the subject, conducting at least one optic perception and interpretation test other than an optic flow test on the subject, recording results of the optic flow test and the at least one optic perception and interpretation test, making a first comparison of the results of the optic flow test against a threshold for optic flow perception, and making a second comparison of the results of the at least one optic perception and interpretation test against a threshold for the at least one optic perception and interpretation test.

Another aspect of the present invention is a method for diagnosing visuospatial disorientation or assessing visuospatial orientation capacity in a subject including conducting an optic flow test on the subject, measuring brain wave responses to record an evoked potential in response to the optic flow test, and comparing the evoked potential against a threshold for optic flow perception.

The present invention also relates to a method for enhancing visuospatial orientation in a subject which includes presenting optic flow stimuli on a device to provide a sense of self-movement.

Figure 6A:
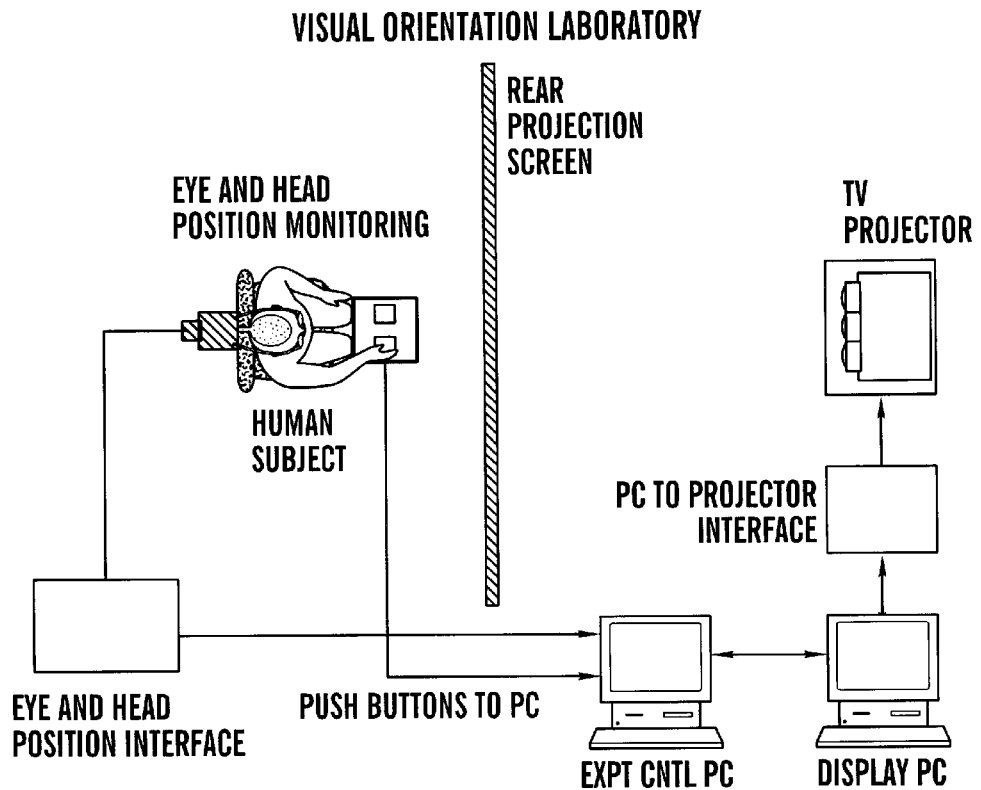
FIGS. 6A–B show schematic diagrams of top (FIG. 5A) and side (FIG. 5B) views of a visual orientation laboratory.
Figure 6B:
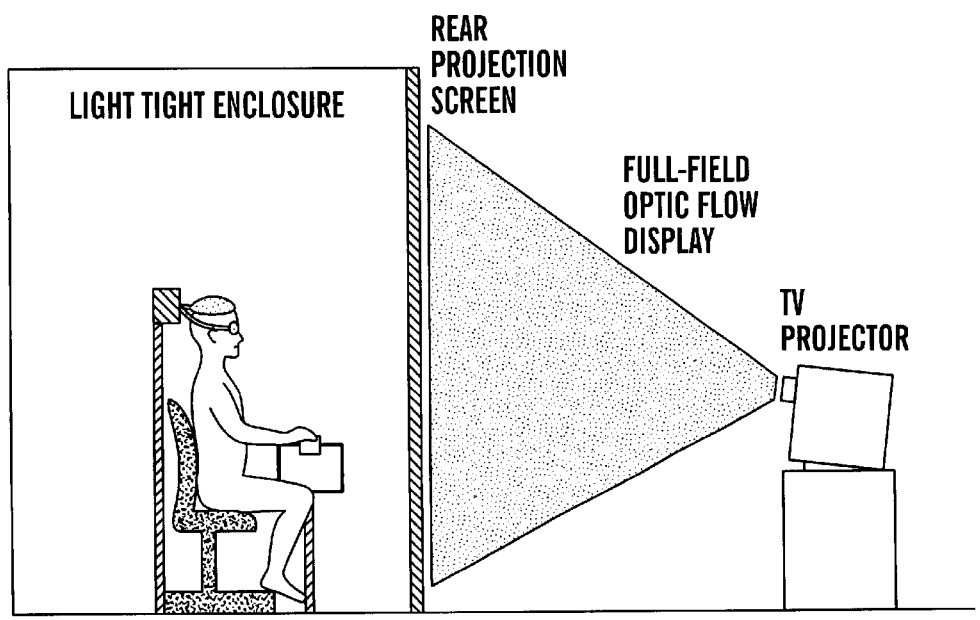

Referring to FIGS. 2E–F, in a preferred embodiment, presenting optic flow stimuli includes providing a sequence of stimuli in which outward radial patterns are superimposed on a background of a device. Preferably, the radial pattern is between 1% and 43% of the viewing, area. The visual stimulus is presented to the subject to provide a sense of self-movement. Referring to FIGS. 6A–B, one example of a device which can be used to present the visual stimuli is a psychophysical chamber which includes a light-tight enclosure with a rear projection screen, a computer display, and response buttons and/or ajoystick. A TV projection system projects animated sequences of white dots on a dark background presented by the visual display computer as specified by the experimental control and computer. The visual stimuli are created off-line by specifically developed algorithms implemented on personal computers. Every dot on the screen in every frame is fully specified by these algorithms. The density of dots is kept constant and homogenous by smoothing every frame. The half-life of a dot is randomly assigned and expired dots are replaced at locations dictated by the density smoothing and movement algorithms. Although one example of a device for presenting the visual stimuli is described, other types of devices for presenting visual stimuli can be used.

Suitable devices include video and computer displays such as a heads-up display, a video game display, a flight simulator, a driving simulator, head-mounted visual display systems, and virtual reality systems. As used herein, a heads-up display includes the view of the environment through a window or cockpit canopy.

EXAMPLES

Example 1

Impaired Visual Perception in the Visuospatial Disorientation of Alzheimer's Disease Subject Selection For Investigation of the Ability of Young Normal, Elderly Normal, and Alzheimer's Disease Patents to Interpret Visual Patterns Young normal (YN), elderly normal (EN), and elderly Alzheimer's Disease (AD) subjects were studied in psychophiysical experiments after evaluating their primary visual and neuropsychological functioning. Subjects were recruited from the University of Rochester or affiliated clinics. Young normal (YN) subjects were undergraduates, or recent graduates, between the ages of 19 and 25 years (mean age=21). Elderly normal (EN) subjects were between the ages of 63–81 years (mean age=72) and were recruited from programs for the healthy elderly or were the spouses of Alzheimer's Disease (AD) subjects. AD subjects were recruited from the clinical programs of the University of Rochester Alzheimer's Disease Center and were between the ages of 60–82 years (mean age=73) with probable AD by National Institute of Neurological and Communicative Disorders and Stroke-Alzheimer's Disease and Related Disorders Association (NINCDS-ADRDA) criteria (McKhaan et al., "Clinical Diagnosis of Alzheimer's Disease: Report of the NINCDS-ADRDA Work Group Under the Auspices of Department of Health and Human Services Task Force on Alzheimer's Disease," *Neurology*, 34:939–944 (1984), which is hereby incorporated by reference).

Informed consent was obtained from all subjects. All protocols were approved by the University of Rochester Human Subjects Review Board.

Each subject was interviewed and examined to exclude persons with neurologic or ophthalmologic disorders other than AD. All subjects had normal, or corrected to normal, visual acuity by Snellen testing (left eye, right eye [mean±SD]: YN=13.7±1.0, 13.7±3.3; EN=19.1±7.3, 19.3±7.8; AD=23.3±10.6, 35.0±25.1) and full visual fields by confrontation testing. Contrast sensitivity profiles were tested at five spatial frequencies (0.5–18 cycles/degree) using a commercial testing system (VisTech Consultants, Inc., Dayton. Ohio). Contrast sensitivity was in the normal range for all groups; the YN group consistently performed better but there were no significant differences between the EN and AD groups (see Table 1, below).

TABLE 1

Results of visual testing for each subject group.

| Test | Snell (OS) | Snell (OD) | Contrast |
|---|---|---|---|
| YN (mn) | 13.7 | 13.7 | 21.7 |

Neuropsychological Testing

Neuropsychological tests were conducted on all subjects, including: the Mini-Mental Status Examination (MMSE) (Folstein et al., "Mini-Mental State: A Practical Method for Grading the Cognitive State of Patients for the Clinician," *J. Psychiat. Res.*, 12:189–198 (1975), which is hereby incorporated by reference), the North American Adult Reading test, the Boston Naming test, the Controlled Oral Word Association (F/A/S) test, the Rey Auditory Verbal Learning test (scored on fifth recall trial), clock drawing (scored by the method of Rouleau (Rouleau et al., "Quantitative and Qualitative Analyses of Clock Drawings in Alzheimer's and Huntington's Disease," *Brain Cogn.*, 18:70–87 (1992), which is hereby incorporated by reference)), the grooved pegboard test (time to complete two rows with the dominant hand), and the Money Road Map test (Money, A Standardized Road Map Test of Direction Sense, San Raphael, Calif., Academic Therapy Publishers (1976), which is hereby incorporated by reference).

The YN and EN groups were normal for age performance on all tasks. The AD group showed uniform, mild impairment on all tasks consistent with the diagnosis of early Alzheimer's Disease (Table 2).

TABLE 2

Results of neuropsychological testing for each subject group.

| Subject group | MMSE, 30 | NART, 32 | Boston, 15 | FAS, 12 | RAVL-5, 15 | Clock, 10 | Pegboard, 2 rows, sec | Road map, 32 | Hooper, 30 | Open field 12 |
|---|---|---|---|---|---|---|---|---|---|---|
| YN* | 29 | 26.3 | 14.7 | 15 | 13.67 | 9.9 | 26.37 | 30 | 27.08 | 10.6 |
|  | (1.1) | (2.9) | (0.52) | (3.95) | (1.75) | (0.2) | (2.28) | (2.1) | (1.5) | (1.34) |
| EN† | 28.5 | 23.4 | 14 | 14.8 | 10.8 | 9.5 | 36.6 | 29.9 | 24.5 | 8.67 |
|  | (1.2) | (4.9) | (0.95) | (4.6) | (3.1) | (0.4) | (8.20) | (2.39) | (2.14) | (3.51) |
| AD‡ | 21.9 | 22.11 | 8.33 | 11.5 | 5.44 | 5.89 | 78.78 | 23.56 | 14.67 | 3.75 |
|  | (3.75) | (7.85) | (3.16) | (2.17) | (2.65) | (2.32) | (53.41) | (4.03) | (6.23) | (1.26) |
| ADN§ | 23.8 | 23.6 | 9.0 | 11.8 | 5.6 | 6.2 | 57.6 | 25.4 | 15.2 | 6.8 |
|  | (0.8) | (8.8) | (2.3) | (2.5) | (1.7) | (1.9) | (13.9) | (2.4) | (5.9) | (2.2) |
| ADI¶ | 20.5 | 18.2 | 7.0 | 11.6 | 5.0 | 5.4 | 113.6 | 20.4 | 12.8 | 4.2 |
|  | (4.4) | (7.8) | (3.8) | (2.3) | (3.4) | (2.6) | (67.8) | (4.6) | (7.0) | (1.3) |

Values in headings are test, best value. Values in table are mean (SD).
*Young normals (YN) (n = 6), mean age = 21 years (range, 19–25).
†Elderly normals (EN) (n = 12), mean age = 72 years (range, 63–81).
‡AD (n = 11), mean age = 73 years (range, 60–82).
§AD with normal thresholds (n = 5), mean age = 72 years (range 65–79).
¶AD with impaired thresholds (ADI) (n = 6), mean age = 72 years (range, 60–82).
MMSE = Mini-Mental State Examination;
NART = North American Reading Test;
Boston = Boston Naming Test;
FAS = Controlled Oral Word Association Test;
RAVL-5 = Rey Auditory Verbal Learning, fifth recall subtest:
Clock = clock drawing; Pegboard = grooved pegboard test (seconds to fill two rows); Road Map = Money Road Map Test; Hooper = Hooper Visual Organization Test;
Open field = open field test of spatial navigation.

TABLE 1-continued

Results of visual testing for each subject group.

| Test | Snell (OS) | Snell (OD) | Contrast |
|---|---|---|---|
| YN (sd) | 1.0 | 3.3 | 14.0 |
| EN (mn) | 19.1 | 19.3 | 25.8 |
| EN (sd) | 7.3 | 7.8 | 14.7 |
| AD (mn) | 23.3 | 35.0 | 31.1 |
| AD (sd) | 10.6 | 25.1 | 9.3 |

YN = young normals (N = 6, mean age = 21 (19–25));
EN = elderly normals (N = 12, mean age = 72 (63–81));
AD = Alzheimer's Disease (N = 11, mean age = 73 (60–82)).

In addition, an open-field test of visuospatial orientation for spatial navigation was developed. Subjects were escorted from the hospital lobby to the laboratory having been told that they would be asked questions about the route when they arrived in the laboratory. This route consisted of walking down four corridors, making four turns, and passing a variety of distinct landmarks. The test consisted of twelve questions that included recognizing the layout of the path, the relative length of each corridor, the direction of turns, and pictures of landmarks.

Visual Psychophysical Testing

Tests of visual discrimination and visual self-movement interpretation both used the same laboratory configuration. Referring to FIGS. 6A–B, the psychophysical chamber was a light-tight enclosure the front wall of which was an 8'×6' rear projection screen. Subjects sat near the center of the enclosure in front of a large screen computer display and used their dominant hand to press one of two response buttons and to manipulate ajoystick to respond in forced choice paradigms. The subjects were seated 4' away from the rear projection tangent screen that covered the central 90°× 74° of the visual field. Centered visual fixation was maintained on a red light emitting diode (LED) image (0.2°). Eye position (electro-oculogram, EOG) and head position were monitored during all trials so that gaze shifts beyond the central segment of the screen aborted that trial. Gaze was restricted to the central 20° in discrimination trials and the central 30° in self-movement interpretation trials so that all foci of expansion in optic flow stimuli were included in the gaze control area. However, all subjects tended to maintain centered fixation on the LED image in all trials.

All experiments were controlled by the REX (real-time experimental) (Hays et al., "A UNIX-Based Multiple Process System for Real-Time Data Acquisition and Control," *WESCON Conf. Proc.*, 2.1–10 (1982), which is hereby incorporated by reference)system running under the UNIX emulating QNX operating system for personal computers. REX controlled the stimulus specifications and presentation, monitored, displayed, and stored head and eye position data, and monitored, displayed, and stored behavioral response data. REX created data filed that included markers for timing of all stimuli and all subject responses. REX also recorded the analog records of eye and head position and laser pointing positioning during all trials.

The left/right discrimination thresholds derived for standardizing visual stimuli across subjects were obtained by an implementation of a PEST algorithm (Pentland, "Maximum Likelihood Estimation: The Best PEST," *Perception & Psychophysics*, 28:377–379 (1980); Harvey, "Efficient Estimation of Sensory Thresholds with ML-PEST," *Spatial Vision*, 11:121–128 (1997), which are hereby incorporated by reference). Each stimulus set consisted of sixty stimuli, two sets of stimuli (left/right signal) logarithmically spaced across the stimulus space (e.g., 100–1000 dots/frame). The algorithm is initially run for 20 trial with a seed value based on previous data about that subject group, the algorithm is then run for another 50 trials based on a seed value that was the estimated threshold from the previous test.

Trials began with an audible tone indicating that central fixation was required within 1 second. A visual stimulus was then presented with the static shape discrimination stimuli being presented for 250 milliseconds (1 msec=0.001 seconds) and the visual motion stimuli being presented for 750 msec. The visual stimuli were followed by a pair of tones to prompt a push button response. The response buttons were then illuminated and the subject was given up to 8 seconds to press the button corresponding to the response chosen for that trial.

Subjects were trained on each task by presenting high coherence stimuli (patterns that were not obscured by superimposed random dots) to test their ability to see those patterns, understand the task, and respond appropriately. Two AD subjects were excluded because they could not perform accurately in the training session. A third AD subject was excluded because button press errors interfered with all of his responses, even with high coherence stimuli.

Visual stimuli were generated off-line and presented by a personal computer driving a television projector (Electrohome 4100, Electrohome Limited, Kitchener, Ontario) to create a 90°×60° image centered at eye height. The stimuli consisted of 500 white dots (2.69 cd/m$^2$) on a black background in an animated sequence of frames presented at 60 Hz. Dot positions were specified for each frame by algorithms for each type of display (Duffy et al, "Sensitivity of MST Neurons to Optic Flow Stimuli. II. Mechanisms of Response Selectivity Revealed by Small-Field Stimuli," *J. Neurophysiol.*, 65:1346–1359 (1991), which is hereby incorporated by reference). All stimuli had the same dot density, luminance, contrast, and average dot speed. Although one example of a system for conducting the test is described, other types of testing systems can be used.

Visual Stimuli

Visual discrimination thresholds were obtained using optic flow stimuli superimposed on random motion. Visual discrimination thresholds for static shapes on a cluttered background, and for horizontal motion on random motion, were obtained to provide measures of more fundamental visual capacities commonly tested in psychophysical research. In these studies, subjects were instructed to push the button labeled as corresponding to the preceding stimulus. Self-movement interpretation was tested based on optic flow using radial stimuli presented without added random motion. In this task the optic flow patterns were made more readily distinguishable by presenting foci of expansion at the usual position ±15° from the center of the display, and at the more extreme positions of ±30°. After each stimulus, four arrows appeared on the screen pointing in the directions of movement simulated by the stimuli. Subjects responded by pressing one of four buttons positioned to correspond to those directions.

In each discrimination task a pseudorandom sequence of stimuli was presented with twelve repetitions at each coherence level. This method of constant stimuli was chosen, rather than more efficient adaptive methods, to obtain the full psychometric function for every subject and stimulus set. The order of presentation for the three stimulus sets was counterbalanced so that approximately equal numbers of subjects in each group did each discrimination task first, second, or third. In the self-movement interpretation task, each of the four directions were presented six times in a pseudorandom order.

Referring to FIGS. 2A–B, in the shape discrimination task dots forming the outline of a circle or a square were centered on the viewing screen and presented with randomly placed stationary dots. Between 1.2% and 11% of the dots were in the shape pattern and subjects chose whether the imbedded pattern formed a circle or a square. In the horizontal motion discrimination task shown in FIGS. 2C and 2D, leftward or rightward moving dots were superimposed on various numbers of dots moving in random directions. Random dot movement was created by randomly assigning each dot, in each frame, either to the patterned motion or to the random motion. Between 1% and 43% of the dots were in the horizontal motion pattern, each stimulus was presented for 750 msec, and subjects chose whether the motion was towards the left or the right. In the optic flow discrimination task shown in FIGS. 2E and 2F, outward radial patterns with a focus of expansion 15° to the left or right of center were superimposed on various numbers of dots moving in random directions. Between 1% and 43% of the dots were in the radial pattern and subjects chose whether the focus of expansion was on the left or the right.

Self-movement interpretation based on optic flow was tested using radial stimuli without added random motion. In this task the optic flow was made more readily distinguishable by presenting foci of expansion at the usual position ±15° from the center of the display, and at the more extreme positions of ±30°. Each stimulus was presented for 750 msec, then four arrows appeared on the screen pointing in the directions of movement simulated by the stimuli. Subjects were instructed to push one of four buttons positioned to correspond to the perceived direction of simulated self-movement. In the self-movement interpretation task, each of the four directions was presented six times.

In tests of visual discrimination, the percentage of dots in the pattern ([pattern dots/pattern plus random dots]* 100) was related to the percentage of correct responses obtained from each subject. These values were fit to a cumulative probability function (Probit function) to derive a perceptual discrimination threshold. Threshold performance was considered the percentage of pattern dots at which subjects achieved 75% correct responses. In tests of self-movement interpretation, all stimuli were presented at 100% coherence and the results were scored as the average percentage of correct responses. Statistical analyses were conducted using the SAS statistical package (SAS Institute, Cary, N.C., SAS Institute I. SAS/STAT User's Guide, Version 6.03, Cary, N.C.: SAS Institute (1988), which is hereby incorporated by reference).

Figure 7:
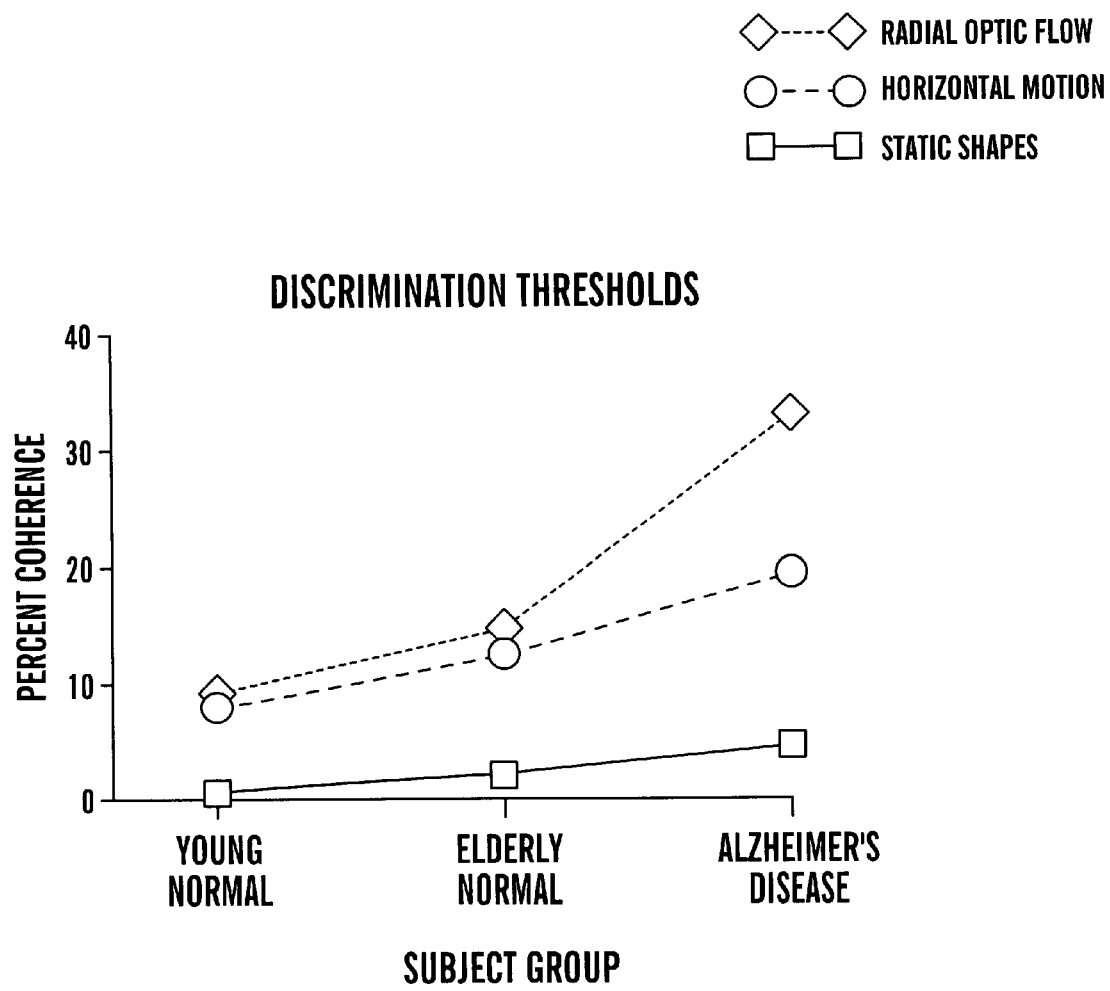
FIG. 7 is a graph showing visual discrimination thresholds from the three stimulus sets in the three subject groups.

Referring to FIG. 7, a selective impairment in optic flow discrimination was seen in Alzheimer's Disease subjects. In this graph, discrimination thresholds (ordinate) are plotted as the percentage of stimulus dots that had to be in the coherent pattern for a subject to correctly identify the target pattern in 75% of the trials (50% correct is chance performance). Data are presented as average thresholds ± the standard error of the mean for each subject group (abscissa): young normals ($N_{YN}$=6), elderly normals ($N_{EN}$=12), and Alzheimer's Disease ($N_{AD}$=11) subjects. Thresholds for the three discrimination tasks are plotted: static shape (squares), horizontal motion (circles), and radial optic flow (diamonds) stimuli. This was confirmed by a two-way analysis of variance (ANOVA) with a significant group-by-task interaction effect (F(4,52)=6.53, p<0.0002). Follow-up linear contrasts determined that the source of the interaction effect was a large difference between horizontal motion and optic flow thresholds in the AD group (ANOVA: F(1,20)=1 5.4, p<0.01) but not in the YN or EN groups. Thus, the first result was that AD patients were selectively impaired in the optic flow discrimination task.

In addition, there was a common trend across all three discrimination tasks with significantly larger thresholds from the AD group. (One-way ANOVAs for: shape F(2,26)= 9.85, p<0.007; horizontal motion F(2,26)=7.27, p<0.003; optic flow F(2,26)=12.9, p<0.0001). All three tasks showed the same pattern of differences such that AD>EN=YN (Tukey's studentized range [HSD] test, p<0.05). There were no significant differences attributable to the order in which static shape, horizontal motion, and optic flow stimulus sets were presented.

Figure 8:
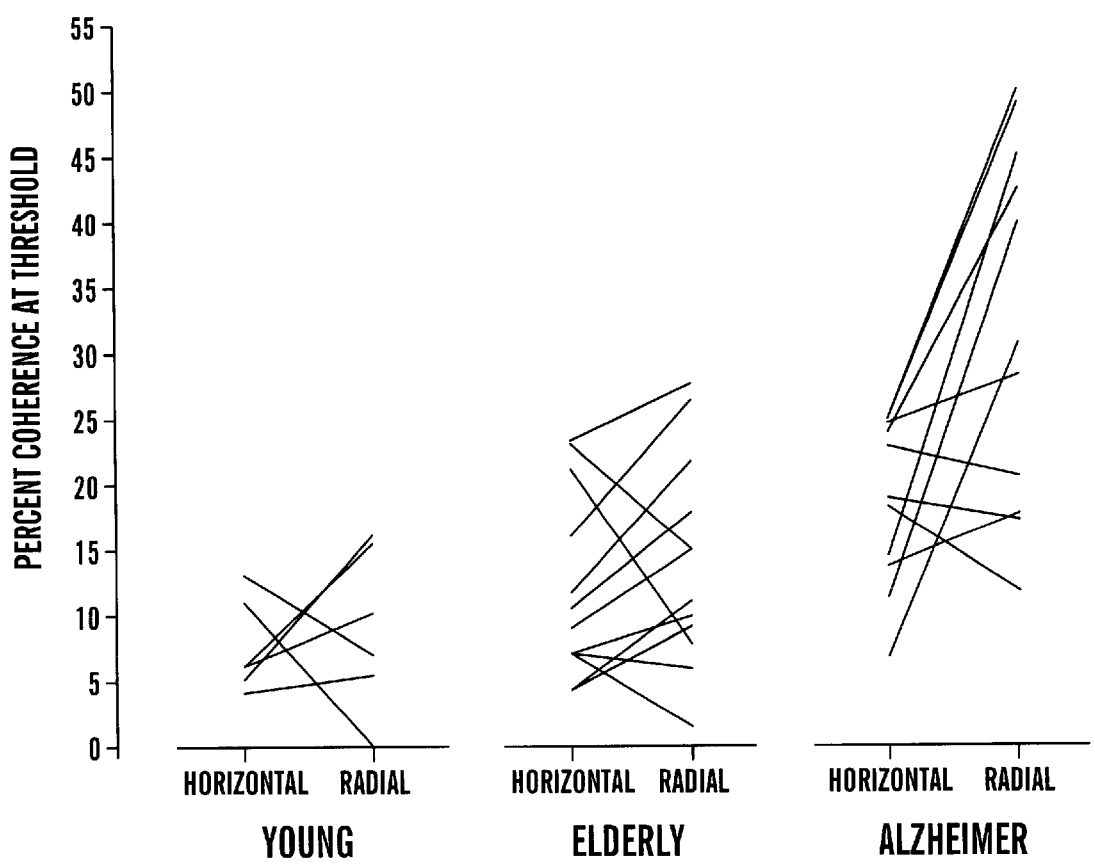
FIG. 8 is a graph showing profile plots of the relationship between horizontal motion and radial optic flow discrimination thresholds.

Referring to FIG. 8, to see if differences between horizontal motion and radial optic flow perception were unique to subjects in the AD group, these thresholds for each subject were compared. Each subject's thresholds are connected by a solid line. Young normal and elderly normal subjects showed relatively small differences between their horizontal motion and radial optic flow thresholds (mean ±SE; young= 1.5±3.5, elderly=2.2±2.2). Alzheimer's subjects showed substantially larger differences between their horizontal motion and radial optic flow thresholds (mean ±SE= 13.6±4.23). This difference was attributable to the fact that six of the subjects (55%, 6/11) showed much larger radial optic flow thresholds with average differences of 25.3±4.0 (bold lines), whereas the remaining five subjects showed small differences between those thresholds (-0.4±3.9). Therefore, the Alzheimer's group consisted of two subgroups: five subjects with approximately equal radial and horizontal thresholds ($T_R$-$T_H$±SE: -0.4±3.9), and six subjects with much larger radial optic flow-thresholds than horizontal motion thresholds ($T_R$-$T_H$±SE:25.3±4.0).

The two groups of AD subjects, defined by the presence or absence of impaired optic flow perception, showed no significant differences in the batters of standard neuropsychological tests of memory and cognitive function. However. regression analysis showed a significant inverse relationship between optic flow threshold and MMSE score (r=-0.53, p<0.05) suggesting that subjects with more advanced AD were more impaired on optic flow perception.

The open-field test of spatial navigation, regarding the route subjects traveled from the hospital lobby to the laboratory, revealed significant between group differences (Table 3).

TABLE 3

| Results of visual testing for each subject group. | | | |
|---|---|---|---|
| AND (mn) | 25.0 | 28.0 | 30.0 |
| AND (sd) | 14.1 | 7.6 | 0 |
| ADI (mn) | 21.3 | 43.8 | 32.5 |
| ADI (sd) | 4.8 | 37.7 | 15.0 |

AND = AD normal thresholds (N = 5, mean age = 72 (765–79)) and impaired;
ADI = AD impaired threshOlds (N = 6, mean age = 72 (60–82)).

Young (N=7) and elderly (N=4) normal subjects averaged 83% and 75% correct responses, respectively, whereas the AD group averaged only 42% correct responses (between group ANOV A F(2,18)=10.38, p<0.01).

Figure 9:
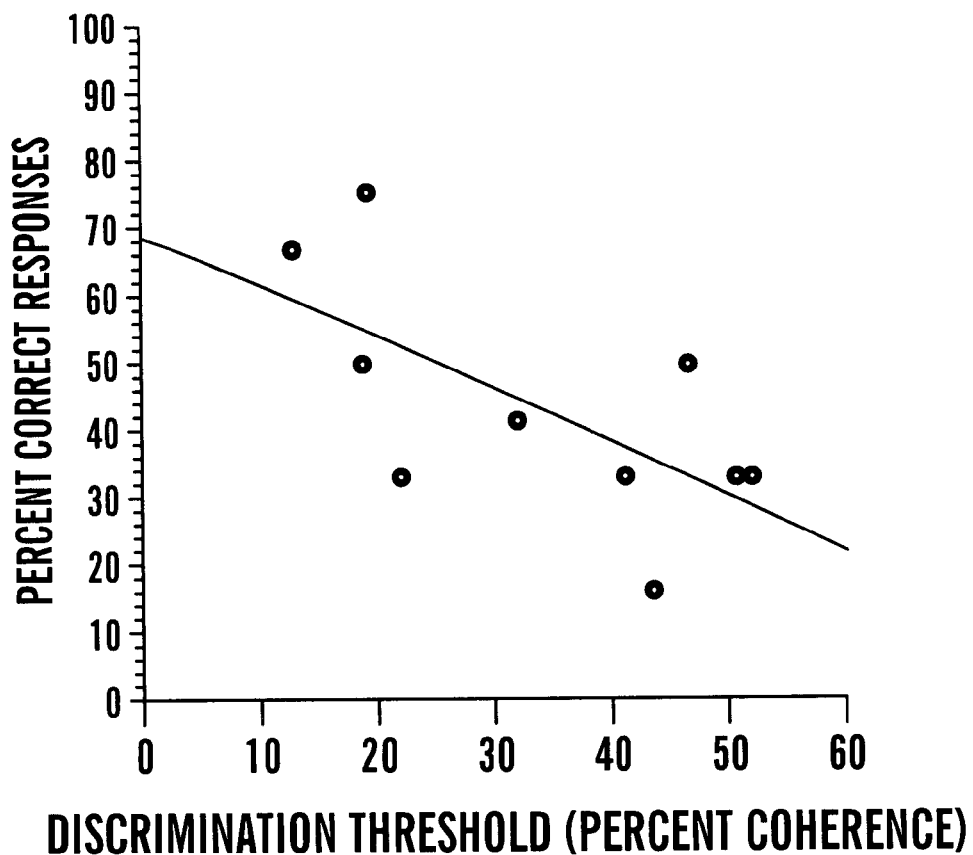
FIG. 9 is a scatter plot showing a relationship between radial optic flow threshold (abscissa) and performance on the spatial navigation test (ordinate)

Referring to FIG. 9, in AD subjects, spatial navigation test scores were significantly correlated with optic flow thresholds, but not with the horizontal motion or shape discrimination thresholds. Poor performance on the spatial navigation test was associated with an elevated optic flow threshold (each point represents the results for one of the ten AD subjects who completed both tests), yielding a best fit line by linear regression with a slope of -0.78 and a correlation coefficient of-0.66 (p<0.05). Multiple regression showed that optic flow threshold accounted for much more of the variance in spatial navigation scores than did horizontal motion or shape discrimination thresholds, with squared semi-partial correlations for optic flow threshold= 0.174, horizontal motion threshold=0.055, and shape discrimination threshold=0.001.

It was considered whether the spatial navigation scores merely reflected global impairment as measured by the MMSE. However, there was no significant correlation between these tests (r=0.11). In addition, there was no benefit to adding MMSE scores to optic flow threshold in a regression model predicting spatial navigation scores. This suggested that optic flow thresholds are a significant, independent predictor of spatial navigation performance.

Optic flow provides cues about self-movement, as well as spatial navigation. It was considered that responses to optic flow might depend on whether the subjects were engaged in a task that was explicitly directed at self-movement interpretation.

Referring to FIGS. 10A–E, optic flow stimuli like those used in the perceptual discrimination tests were used, but the subjects were asked to indicate the simulated direction of self-movement rather than the side of the focus of expansion. The perceptual limitations of elevated optic flow thresholds were overcome by eliminating random dot motion from the stimuli and by presenting foci of expansion at the usual positions of ±15° and also at ±30°. Subjects responded by indicating the direction of self-movement that had been simulated by the stimulus.

Figure 10A:
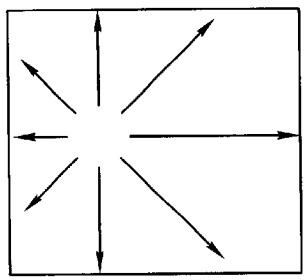
FIGS. 10A–E show studies of the ability to interpret optic flow as simulating self-movement conducted in young normal (YN), elderly normal (EN), and Alzheimer's subjects who were normal (ADN) or impaired (ADI) by optic flow discrimination testing.
Figure 10B:
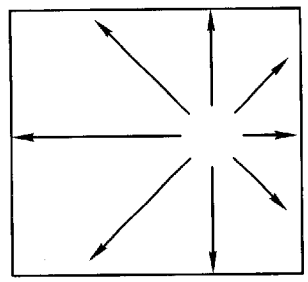
Figure 10C:
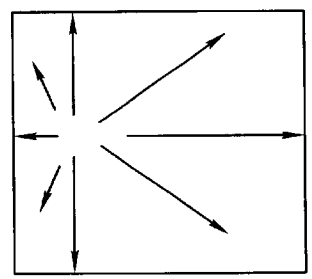
Figure 10D:
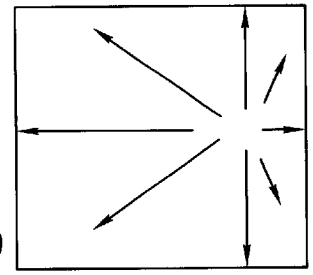
Figure 10E:
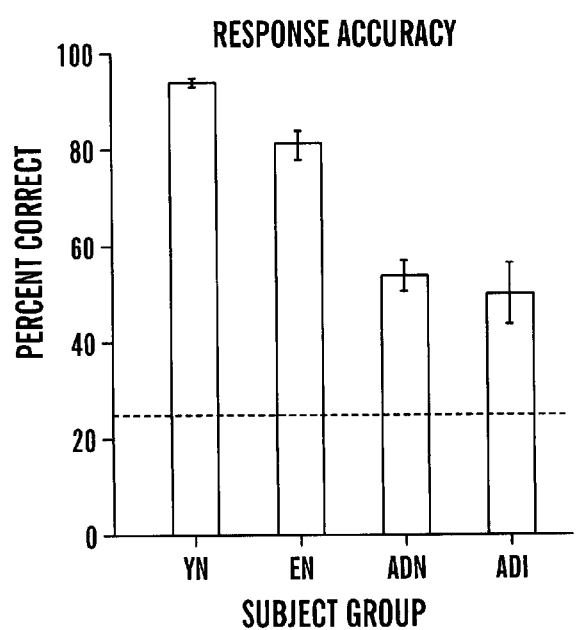
Figure 11A:
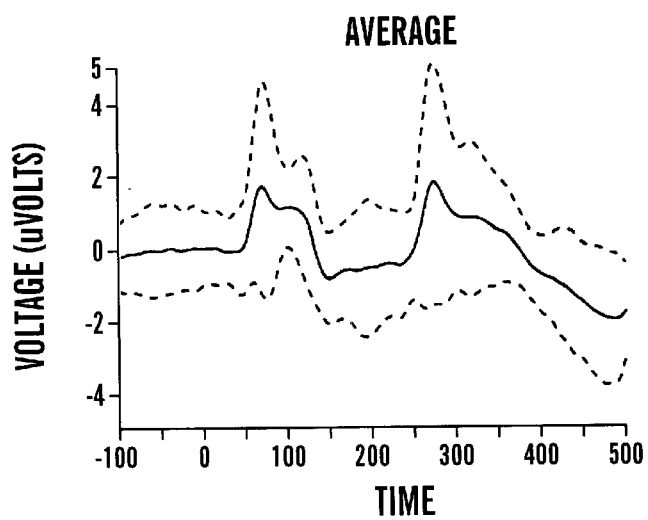
FIGS. 11A–F show the average evoked responses recorded from the scalps of eight young normal subjects in response to 222 presentations of alternating inward and outward radial optic flow patterns.
Figure 11B:
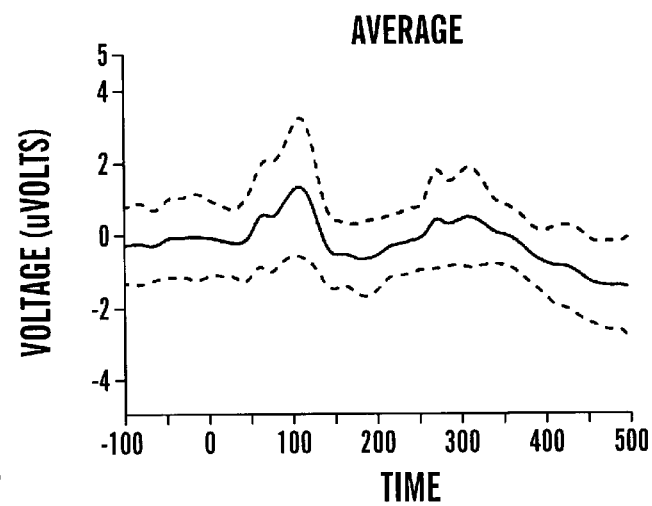
Figure 11C:
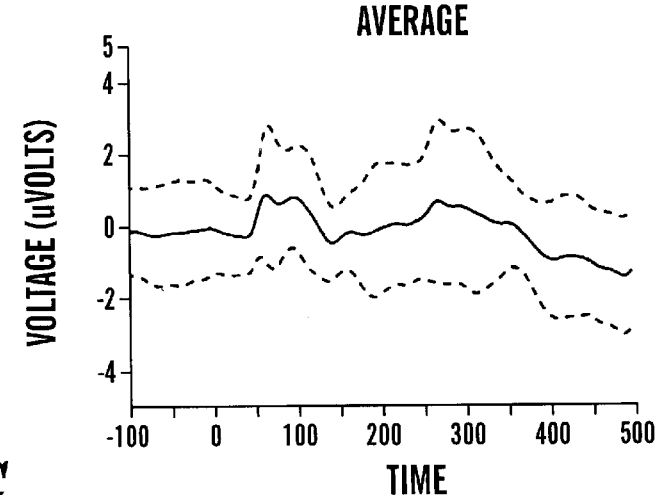
Figure 11D:
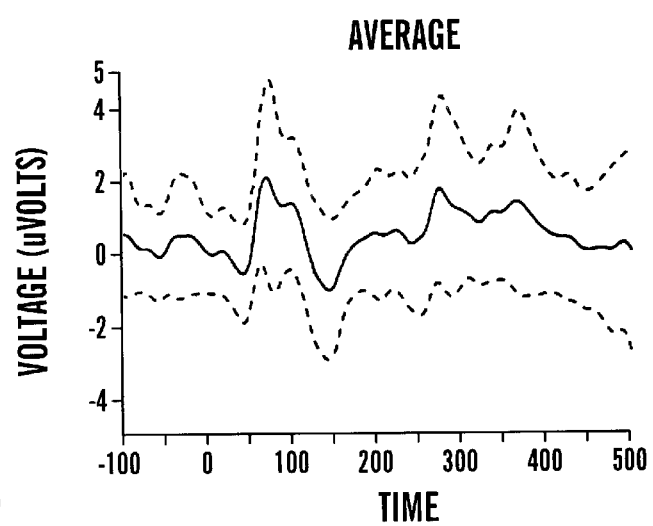
Figure 11E:
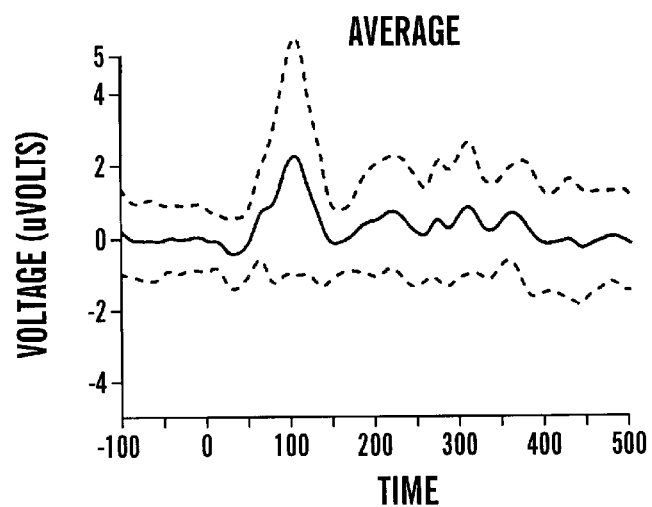
Figure 11F:
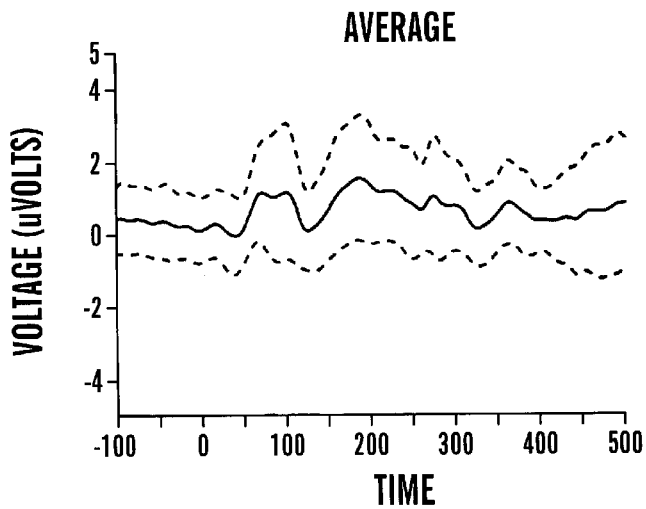
Figure 12A:
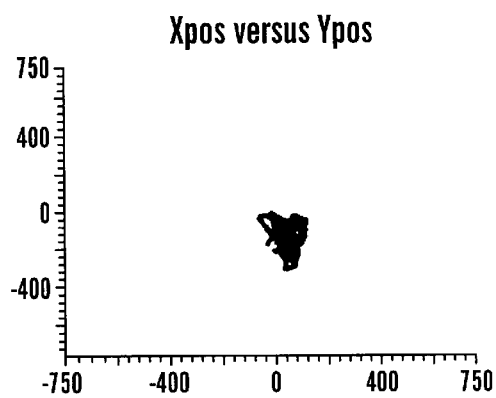
FIGS. 12A–D are graphs showing posture tracings from an elderly normal and Lewy Body disease patient (posture here in force plate units).
Figure 12B:
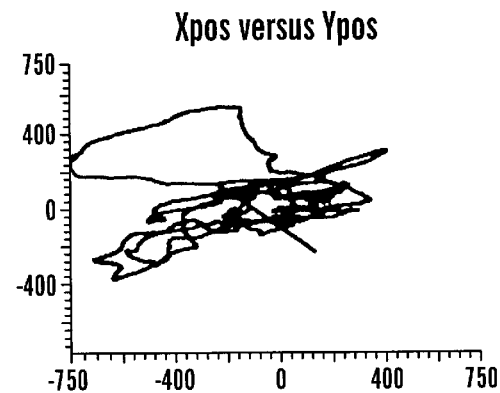
Figure 12C:
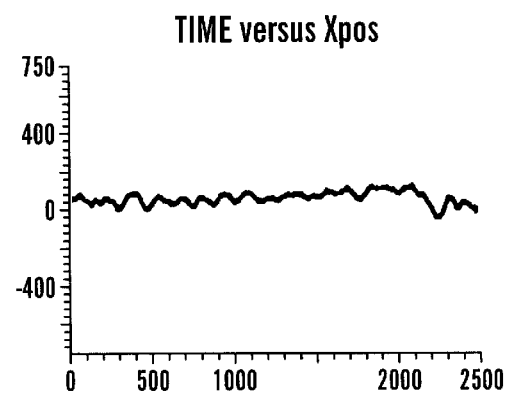
Figure 12D:
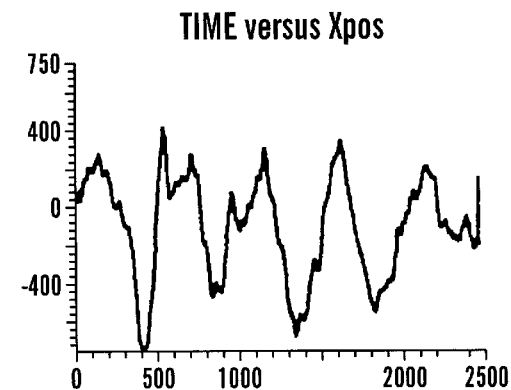

Referring to FIGS. 10A–D, radial optic flow stimuli were presented at 100% coherence with foci of expansion at ±15° or ±30° with subjects choosing which of four directions corresponded to the direction simulated by the stimulus. Referring to FIG. 10E, the percent correct identifications of the direction simulated in the stimulus (ordinate) for each subject group (abscissa) (mean ±SD: $N_{YN}=6$, $N_{EN}=11$, $N_{ADN}=5$, and $N_{ADI}=6$) is shown. The graph shows the percent correct identifications averaged across all four stimuli (chance performance=25% correct).

The results of self-movement interpretation were compiled for the young normal (YN) and elderly normal (EN) groups. AD subjects were split into Alzheimer's normals (ADN) and Alzheimer's impaired (ADI) subgroups based on their optic flow thresholds. Significant differences between subject groups were found (ANOVA: $F(3,24)=26.0$; $P<0.0001$) with the average percent correct responses decreasing from YN=94% and EN=81% to ADN=54% and ADI=50% (Tukey's HSD test showed that YN=EN>ADN= ADI, $p<0.05$). Thus, young and elderly normal subjects did uniformly well on self-movement interpretation, and all Alzheimer's subjects did poorly at self-movement interpretation.

The ADN and ADI groups were similarly impaired on self-movement interpretation, so this impairment was not a function of optic flow discrimination threshold. This was confirmed by the absence of a correlation between self-movement scores and optic flow thresholds in the AD group ($r=0.01$). Furthermore, three AD subjects spontaneously complained that the stimuli did not suggest self-movement although they could point at the focus of expansion.

Referring to FIGS. 3A–D, two delayed match to sample experiments were conducted in a small number of subjects as a preliminary test of visual recognition memory. In each experiment a visual stimulus (100% coherence) was presented for 100 msec, the screen was then blank for a varying period (250–750 msec), and then a second visual stimulus was presented. The subject was then asked if the second stimulus was the same or different from the first as a 2-alternative forced choice (2AFC) task. Referring to FIG. 3A, the first experiment tested visual shape recognition (circles or squares). Referring to FIG. 3B, the second experiment tested the ability to recognize optic flow stimuli with the center-of-motion (COM) shifted by 15° to the left or right of center.

Figure 3C:
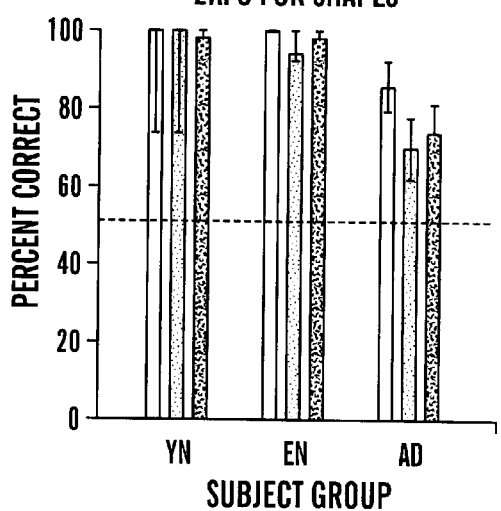
Figure 3D:
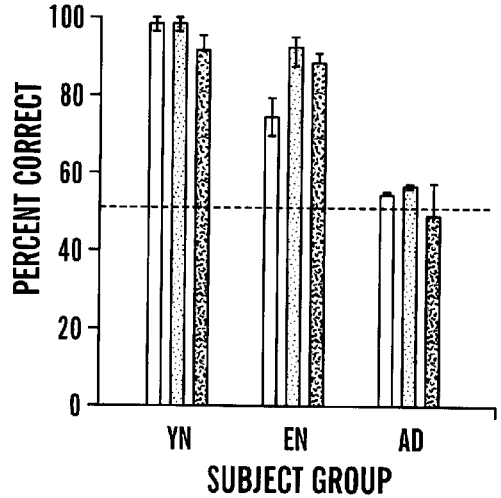

FIG. 3C shows results for the delayed match to sample for shapes with only the AD group showing worsening performance with increasing interstimulus intervals. The results are given as percent correct responses of whether the first and second stimuli were the same or different for young (YN, N=3), elderly (EN, N=3), and Alzheimer's (AD, N=3) subjects. Referring to FIG. 3D, delayed match-to-sample for optic flow stimuli also showed a significant croup main effect ($p<0.01$), with excellent performance from young and elderly subjects but near chance performance from Alzheimer's subjects.

These studies showed that young and elderly normal subjects show excellent performance in visual delayed match to sample paradigms with high coherence visual stimuli. The fact that AD subjects were impaired in both tasks, provides evidence for a more general impairment of visual working memory, and the finding of a more profound deficit in optic flow memory than in shape memory suggests that there may be stimulus specific effects.

Referring to FIGS. 4A–F, three experiments tested the ability of young normal subjects to use optic flow stimuli to point toward the simulated heading in a preceding stimulus. In these experiments, a series of optic flow stimuli with centers of motion (COM) located along the horizontal meridian was presented. The optic flow stimuli were presented in three conditions: 1) 100% coherence, 2) 50% stationary random dots, or 3) 50% moving random dots. The stimuli were presented for 1 second. The subjects then used ajoystick pointer to position a red laser spot at the perceived location of the COM in the preceding stimulus.

Figure 4A:
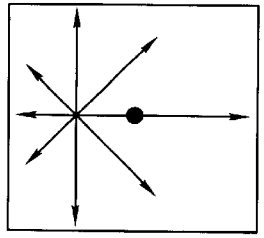
FIGS. 4A–G show optic flow stimuli and results for optic flow remembered heading tests.
Figure 4B:
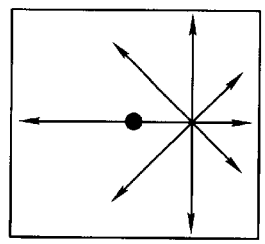
Figure 4C:
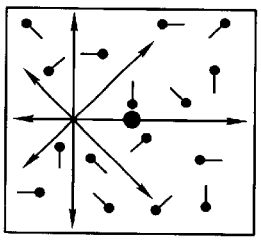
Figure 4D:
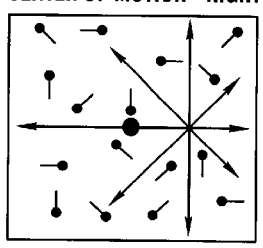
Figure 4E:
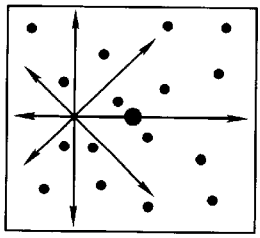
Figure 4F:
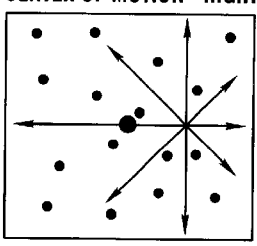
Figure 4G:
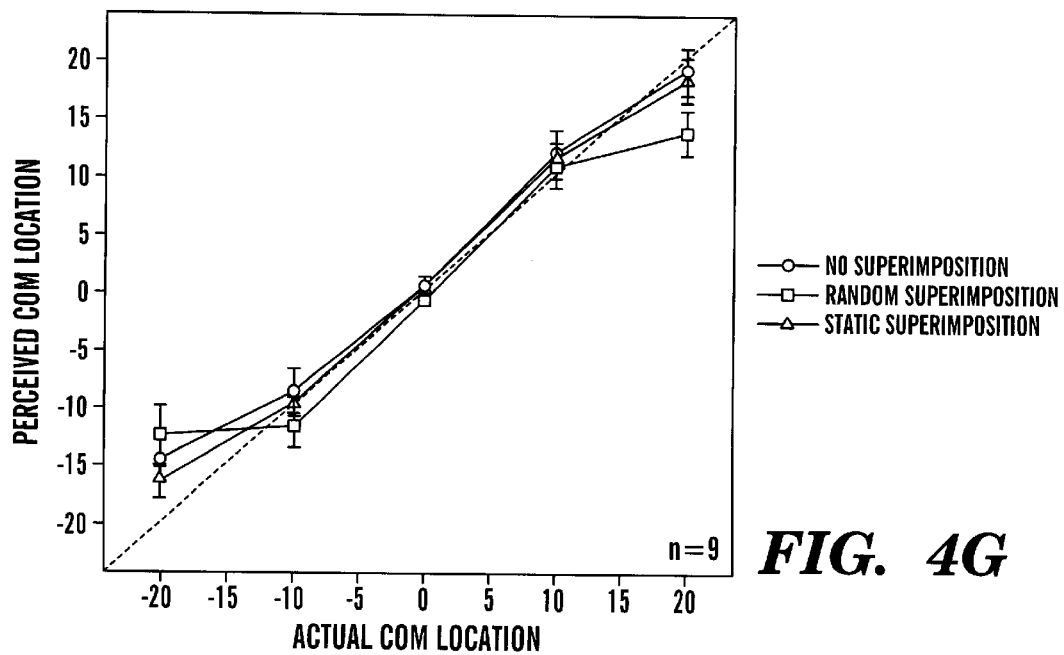

Referring to FIG. 4G, the results of these studies as plots of the remembered COM versus the actual location of the COM in the preceding stimulus are shown. In all conditions, the subjects showed excellent performance with the remembered COM location closely approximating actual location. ANOVA showed no significant differences between performance with superimposed stationary or moving dots. However, there may be some tendency for the most eccentric COMs to be seen as being closer to the center with the random movement patterns.

These experiments show that normal subjects can use optic flow in a task that requires pointing to the remembered COM.

Impaired Optic Flow Perception in AD

Visual perception in AD was studied (see discussion above), finding impaired ability to see optic flow, the radial patterns of visual motion that result from self-movement (see FIG. 1). Thus, AD is not merely a memory disorder with aphasia, agnosia, and apraxia. It is also a perceptual disorder with impairments that may present as spatial disorientation.

A trend toward impaired horizontal motion perception in normal elderly (Gilmore et al., "Motion Perception and Aging," *Psychol. Aging*, 7:654–660 (1992), which is hereby incorporated by reference) and AD subjects (Trick et al., "Visual Sensitivity to Motion: Age-Related Changes and Deficits in Senile Dementia of the Alzheimer's Type," *Neurology*, 41:1437–1440 (1991), which is hereby incorporated by reference) was found, and it was found that this impairment is associated with a decreased MMSE score. Combined with the lack of an association with visual acuity or contrast sensitivity, this supports the conclusion that visual discrimination impairments in AD reflect defects of central visual processing (Silverman et al., "Dissociation Between the Detection and Perception of Motion in Alzheimer's Disease," *Neurology*, 44:1814–1818 (1994), which is hereby incorporated by reference).

Comparisons between horizontal motion and optic flow perception revealed a much larger impairment of optic flow perception in AD patients. Referring to FIGS. 2A–F, the AD group showed much larger optic flow thresholds than horizontal motion thresholds, whereas the YN and EN groups had similar thresholds with both stimulus sets. Referring to FIG. 7, impaired optic flow discrimination was limited to six of the eleven AD subjects (55%). These optic flow impaired AD subjects were not significantly different from other AD subjects by a variety of visual and neuropsychological measures (Tables 2 and 3).

Perceptual Mechanisms of Visuospatial Disorientation

Referring to FIG. 8, a clear association was found between impaired optic flow perception in AD and the inability to answer questions about a recently traversed route through a complex environment as measured by an open-field test of spatial navigation. This finding supports the relevance of optic flow perception to visuospatial orientation and the possibility that impaired optic flow analysis might contribute to visuospatial disorientation. The prevalence of this impairment in the AD subjects (55%) is somewhat higher than previous estimates of the prevalence of visuospatial disorientation in AD (20–40%) (Henderson et al., "Spatial Disorientation in Alzheimer's Disease," *Arch. Neurol.*, 46:391–394 (1989); Mendola et al., "Prevalence of Visual Deficits in Alzheimer's Disease," *Optometry and Vision Science*, 72:155–167 (1995), which are hereby incorporated by reference). This difference may be attributable to greater sensitivity of the above psychophysical measures compared to the insensitivity of standard neuropsychological tests of visuospatial function in early AD. One implication is that tests of visual perception might detect impaired spatial processing before it would be evident in other tests.

In a separate task, readily discriminated optic flow stimuli (100% motion coherence and widely separated foci of expansion) were used to test the subject's ability to interpret optic flow as a cue about self-movement. As shown in FIG. 8, a significant impairment of optic flow interpretation was found in AD subjects that was not correlated with their optic flow discrimination thresholds or their performance on other visual and neuropsychological tests. The elderly normal subjects showed a trend towards impaired optic flow interpretation that was consistent with the previous report of impaired heading detection in elderly subjects viewing optic flow simulations of self-movement (Warren et al., "Age Differences in Perceiving the Direction of Self-Motion From Optical Flow," *Journal of Gerontology*, 44:147–153 (1989), which is hereby incorporated by reference). However, only the AD group was significantly different from the YN group.

These findings suggested a degree of independence between optic flow perception for spatial navigation and optic flow interpretation as a cue about self-movement. This was highlighted by the spontaneous complaints from three AD subjects who could see optic flow, but could not see how it implied anything about self-movement. The inability to recognize the patterned visual motion of optic flow as a cue about self-movement might be termed visual autokineagnosia (VAKA). This is consistent with the nomenclature for visual agnosias based on the presence of an interpretive deficit with preserved perception (Damasio, "Disorders of Complex Visual Processing: Agnosias, Achromotopsia, Balint's Syndrome, and Related Difficulties of Orientation and Construction," In: *Principles of Behavioral Neurology*, Mesulam, ed., Philadelphia, Davis, pp. 259–288 (1985), which is hereby incorporated by reference). In addition, this term emphasizes that this mechanism might contribute to visuospatial disorientation from other causes including focal cortical lesions or other neurodegenerative diseases. The symptoms of visuospatial disorientation may be more evident in AD because spatial memory impairments in these patients place greater reliance on visual perceptual and interpretive capacities.

Localizing Visuospatial Disorientation

The findings described above were consistent with the dual pathways model of extrastriate visual cortex. This model was embedded in Kleist's assigning object agnosias to occipito-temporal areas and spatial agnosias to occipito-parietal areas (Kleist (Kleist, *Gehimpathologie*, Leipzig, Barth (1934), which is hereby incorporated by reference) as cited in Grusser (Grusser et al., "Visual Agnosias and Other Disturbances of Visual Perception and Cognition," 1$^{st}$ed., Boston, CRC Press (1991), which is hereby incorporated by reference)). Ungerleider and Mishkin (Ungerleider et al., "Two Cortical Visual Systems," In: *Analysis of Visual Behavior*, Ingle et al., eds., Cambridge, MIT Press, pp. 549–586 (1982), which is hereby incorporated by reference) developed this model by describing a ventral, occipito-temporal pathway for visual object recognition and a dorsal, occipito.-parietal pathway for visuospatial perception based on lesion studies in monkeys, with Goodale and Milner (Goodale et al., "Separate Visual Pathways for Perception and Action," *Trends in Neurosci.*, 15:20–25 (1992), which is hereby incorporated by reference) emphasizing the behavioral consequences of this organization.

The dorsal visual pathway for visuospatial processing contains areas devoted to visual motion processing, with the middle temporal area (MT) playing a critical role in the perception of uniform patterns of visual motion (Duffy et al., "Medial Superior Temporal Area Neurons Respond to Speed Patterns in Optic Flow," *J. Neurosci.*, 17:2839–2851 (1997), which is hereby incorporated by reference). The adjacent medial superior temporal area (MST) processes optic flow (Duffy et al., "Sensitivity of MST Neurons to Optic Flow Stimuli. II. Mechanisms of Response Selectivity Revealed By Small-Field Stimuli," *J. Neurophysiol.*, 65:1346–1359 (1991), which is hereby incorporated by reference) and its cues about heading direction (Duffy et al., "Response of Monkey MST Neurons to Optic Flow Stimuli With Shifted Centers of Motion." *J. Neurosci.*, 15:5192–5208 (1995), which is hereby incorporated by reference) and environmental structure (Schaefsma et al., "Neurons in the Ventral Intraparietal Area of Awake Macaque Monkey- Closely Resemble Neurons in the Dorsal Part of the Medial Superior Temporal Area in Their Responses to Optic Flow," *J. Neurophysiol.*, 76:4056–4068 (1996), which is hereby incorporated by reference) with contributions from other sites along the dorsal pathway (Schaefsma et al., "Neurons in the Ventral Intraparietal Area of Awake Macaque Monkey Closely Resemble Neurons in the Dorsal Part of the Medial Superior Temporal Area in Their Responses to Optic Flow," *J. Neurophvsiol.*, 76:4056–4068 (1996); Siegel et al., "Analysis of Optic Flow in the Monkey Parietal Area 7a," *Cerebral Cortex*, 7:327–346 (1997), which are hereby incorporated by reference). This suggests that disease activity in the area MT might account for elevated horizontal motion thresholds in AD (Gilmore et al., "Motion Perception and Alzheimer's Disease." *J. Gerontol.*, 49:P52–P57 (1994), which is hereby incorporated by reference), whereas the elevated optic flow thresholds found above might reflect effects on area MST. Likewise. the separate impairment of optic flow interpretation, seen in some AD subjects, might be attributable to disease effects on higher dorsal visual areas.

Rather than explaining these deficits as the result of focal pathology, they might be viewed as cortical disconnection syndromes. This is consistent with the selective effects of AD on the corticocortical projection neurons (Hof et al., "Selective Disconnection of Specific Visual Association Pathways in Cases of Alzheimer's Disease Presenting with Balint's Syndrome," *J. Neuropathol. Exp. Neurol.*, 49:168–184 (1990), which is hereby incorporated by reference) that might cause greater deterioration of visual motion signals as they pass through the successive stages of the dorsal visual pathway. Thus, increasing impairment in horizontal motion, optic flow, and self-movement perception could reflect the cumulative degradation of visual motion signals so that lower centers are least affected and higher centers are most affected. Thus visuospatial disorientation in AD might suggest a new model for cortical pathophysiology: the serial disconnection syndrome.

Example 2

Evoked Responses

Optic flow test results and optic perception and interpretation test results can be recorded as evoked responses. This method involves placing electrodes on the scalp of a subject to record brain wave responses, presenting visual stimuli, and averaging the recorded brain wave responses.

Referring to FIG. 11, evoked responses were recorded from the scalps of eight young normal subjects in response to 222 presentations of alternating inward and outward radial optic flow patterns. The results were then averaged. Solid lines are the average, dashed lines are ±1 standard deviation. Stimulus onset was at time=0. The main response was at approximately 100 msec later. A second response 250 msec after that was to the stopping of the movement.

Although one example of recording test results as evoked responses for normal subjects is described above, other subjects (e.g., EN or AD) and other methods of recording evoked responses can be used.

Example 3

Evaluation of Visual-Postural Reflexes

It was hypothesized that visuo-postural reflexes might differentiate Alzheimer's disease (AD) from Lewy Body disease (LBD). Specifically, that AD causes diminished visuo-postural reflexes and LBD causes enhanced visuo-postural reflexes. Two preliminary results are relevant. First, psychophysical studies showing that early AD is associated with impaired perception of the visual motion in optic flow that stabilizes posture. Second, posturographic studies showing that LBD causes an exaggeration of visuo-postural reflexes, like that seen in Parkinson's disease (PD).

Referring to FIGS. 12A–D, postural responses to optic flow stimuli were recorded using a postural force plate that was placed 1 meter from a 6 ft×9 ft video projection screen. An elderly normal subject and an LBD patient were recorded while viewing circular (shown in FIGS. 12A–D) and radial optic flow stimuli. It was found that the LBD patient showed exaggerated postural responses to the visual motion stimuli. His greatest postural responses were to circular motion with large sway amplitude (top) and sway entrainment at the frequency (2 Hz) of the alternating clockwise-counterclockwise stimulus.

This suggested that LBD may cause the same type of exaggerated postural responses to visual stimuli that have been seen in Parkinson's disease. More particularly, optic flow has a powerful influence on postural control that becomes increasingly dominant in aging. The neurological and neuropathological similarities between PD and Lewy Body disease (LBD) suggest that the latter group might share the visuo-postural characteristics of the former.

Further, sensitive measures of visuo-postural function may be used to differentiate between early AD and early LBD. The former group might not respond because they do not process the visual stimuli and the latter group might be excessively responsive to those stimuli. More particularly, patients with Alzheimer s disease (AD) show postural instability only when confronted with unstable support surfaces with fall risks that are not clearly related to scores on a variety of cognitive tests (Alexander et al., "Maintenance of Balance, Gait Patterns, and Obstacle Clearance in Alzhiemer's Disease," *Neurology*, 45:908–914 (1995), which is hereby incorporated by reference). However, AD also causes an impairment of visual motion processing of optic flow that could blunt visuo-postural reflexes.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for diagnosing visuospatial disorientation or assessing visuospatial orientation capacity in a subject comprising:
   conducting an optic flow test on the subject;
   recording results of the optic flow test; and
   comparing the results of the optic flow test against a threshold for optic flow perception.

2. The method as set forth in claim 1 wherein the optic flow test is an optic flow discrimination test.

3. The method as set forth in claim 1 wherein the optic flow test is a visual self-movement interpretation test.

4. The method as set forth in claim 1 wherein the optic flow test is an optic flow delayed match test.

5. The method as set forth in claim 1 wherein the optic flow test is an optic flow remembered heading test.

6. The method as set forth in claim 1 wherein the recording comprises measuring brain wave responses to record an evoked potential in response to the optic flow test.

7. The method as set forth in claim 1 further comprising:
   correlating the comparison with a profile for a neurodegenerative disorder to diagnose the neurodegenerative disorder.

8. The method as set forth in claim 7 wherein the neurodegenerative disorder is selected from the group consisting of Alzheimer's disease, Parkinson's disease, Lewy Body disease, stroke, traumatic brain injury, focal tumors, and focal malformations.

9. The method as set forth in claim 1 further comprising:
   conducting at least one optic perception and interpretation test other than an optic flow test on the subject;
   recording results of the at least one optic perception and interpretation test; and
   comparing the results of the at least one optic perception and interpretation test against a threshold for the at least one optic perception and interpretation test.

10. The method as set forth in claim 9 wherein the recording comprises measuring brain wave responses to record an evoked potential in response to the at least one optic perception and interpretation test.

11. The method as set forth in claim 9 wherein the at least one optic perception and interpretation test is a test of spatial navigation.

12. The method as set forth in claim 9 wherein the at least one optic perception and interpretation test is a shape discrimination test.

13. The method as set forth in claim 9 wherein the at least one optic perception and interpretation test is a horizontal motion discrimination test.

14. The method as set forth in claim 9 wherein the at least one optic perception and interpretation test is a visuo-postural reflex test.

15. The method as set forth in claim 9 wherein the at least one optic perception and interpretation test is an object vision test.

16. The method as set forth in claim 9 further comprising:
   correlating the comparison with a profile for a neurodegenerative disorder to diagnose the neurodegenerative disorder.

17. The method as set forth in claim 16 wherein the neurodegenerative disorder is selected from the group consisting of Alzheimer's disease, Parkinson's disease, Lewy Body disease, stroke, traumatic brain injury, focal tumors, and focal malformations.

18. A method for diagnosing visuospatial disorientation or assessing visuospatial orientation capacity in a subject comprising:

conducting an optic flow test on the subject;

conducting at least one optic perception and interpretation test other than an optic flow test on the subject;

recording results of the optic flow test and the at least one optic perception and interpretation test;

making a first comparison of the results of the optic flow test against a threshold for optic flow perception; and making a second comparison of the results of the at least one optic perception and interpretation test against a threshold for the at least one optic perception and interpretation test.

19. The method as set forth in claim 18 wherein the optic flow test is an optic flow discrimination test.

20. The method as set forth in claim 18 wherein the optic flow test is a visual self-movement interpretation test.

21. The method as set forth in claim 18 wherein the optic flow test is an optic flow delayed match test.

22. The method as set forth in claim 18 wherein the optic flow test is an optic flow remembered heading test.

23. The method as set forth in claim 18 wherein the recording comprises measuring brain wave responses to record an evoked potential in response to the optic flow test and the at least one optic perception and interpretation test.

24. The method as set forth in claim 18 further comprising:

correlating the first and second comparison with a profile for a neurodegenerative disorder to diagnose the neurodegenerative disorder.

25. The method as set forth in claim 24 wherein the neurodegenerative disorder is selected from the group consisting of Alzheimer's disease, Parkinson's disease, Lewy Body disease, stroke, traumatic brain injury, focal tumors, and focal malformations.

26. The method as set forth in claim 18 wherein the at least one optic perception and interpretation test is a test of spatial navigation.

27. The method as set forth in claim 18 wherein the at least one optic perception and interpretation test is a shape discrimination test.

28. The method as set forth in claim 18 wherein the at least one optic perception and interpretation test is a horizontal motion discrimination test.

29. The method as set forth in claim 18 wherein the at least one optic perception and interpretation test is a visuopostural reflex test.

30. The method as set forth in claim 18 wherein the at least on optic perception and interpretation test is an object vision test.

31. A method for diagnosing visuospatial disorientation or assessing visuospatial orientation capacity in a subject comprising:

conducting an optic flow test on the subject;

measuring brain wave responses to record an evoked potential in response to the optic flow test; and comparing the evoked potential against a threshold for optic flow perception.

32. The method as set forth in claim 31 wherein the optic flow test is an optic flow discrimination test.

33. The method as set forth in claim 31 wherein the optic flow test is a visual self-movement interpretation test.

34. The method as set forth in claim 31 wherein the optic flow test is an optic flow delayed match test.

35. The method as set forth in claim 31 wherein the optic flow test is an optic flow remembered heading test.

36. The method as set forth in claim 31 further comprising:

correlating the comparison with a profile for a neurodegenerative disorder to diagnose the neurodegenerative disorder.

37. The method as set forth in claim 36 wherein the neurodegenerative disorder is selected from the group consisting of Alzheimer's disease, Parkinson's disease, Lewy Body disease, stroke, traumatic brain injury, focal tumors, and focal malformations.

38. The method as set forth in claim 31 further comprising:

conducting at least one optic perception and interpretation test other than an optic flow test on the subject;

measuring brain wave responses to record an evoked potential in response to the at least one optic perception and interpretation test; and comparing the results of the at least one optic perception and interpretation test against a threshold for the at least one optic perception and interpretation test.

39. The method as set forth in claim 38 wherein the at least one optic perception and interpretation test is a test of spatial navigation.

40. The method as set forth in claim 38 wherein the at least one optic perception and interpretation test is a shape discrimination test.

41. The method as set forth in claim 38 wherein the at least one optic perception and interpretation test is a horizontal motion discrimination test.

42. The method as set forth in claim 38 wherein the at least one optic perception and interpretation test is a visuopostural reflex test.

43. The method as set forth in claim 38 wherein the at least one optic perception and interpretation test is an object vision test.

44. The method as set forth in claim 38 further comprising:

correlating the comparison with a profile for a neurodegenerative disorder to diagnose a neurodegenerative disorder.

45. The method as set forth in claim 44 wherein the neurodegenerative disorder is selected from the group consisting of Alzheimer's disease, Parkinson's disease, Lewy Body disease, stroke, traumatic brain injury, focal tumors, and focal malformations.

* * * * *